(12) United States Patent
Wang et al.

(10) Patent No.: US 8,916,574 B2
(45) Date of Patent: Dec. 23, 2014

(54) 4-(SUBSTITUTED ANILINO)-QUINAZOLINE DERIVATIVES USEFUL AS TYROSINE KINASE INHIBITORS

(75) Inventors: Jingyi Wang, Shandong (CN); Chuanwen Fan, Shandong (CN); Long Zhang, Shandong (CN); Zhongru Guo, Beijing (CN); Ying Li, Gansu (CN); Shaobo Yang, Shandong (CN); Shousheng Yan, Shandong (CN); Jianrong Zhu, Gansu (CN); Qingmin Yang, Shandong (CN); Minghui Zhang, Shandong (CN)

(73) Assignee: Qilu Pharmaceutical Co., Ltd., Jinan, Shangdong (CN)

(*) Notice: Subject to any disclaimer, the term of this patent is extended or adjusted under 35 U.S.C. 154(b) by 120 days.

(21) Appl. No.: 13/498,547

(22) PCT Filed: Sep. 20, 2010

(86) PCT No.: PCT/CN2010/001449
§ 371 (c)(1),
(2), (4) Date: Apr. 27, 2012

(87) PCT Pub. No.: WO2011/035540
PCT Pub. Date: Mar. 31, 2011

(65) Prior Publication Data
US 2012/0208833 A1    Aug. 16, 2012

(30) Foreign Application Priority Data

Sep. 28, 2009  (CN) .......................... 2009 1 0177401

(51) Int. Cl.
| | | |
|---|---|---|
| A01N 43/54 | (2006.01) | |
| A61K 31/517 | (2006.01) | |
| C07D 239/72 | (2006.01) | |
| C07D 401/00 | (2006.01) | |

(52) U.S. Cl.
USPC .................... 514/266.2; 514/266.1; 544/283; 544/284

(58) Field of Classification Search
USPC ..................... 514/266.1, 266.2; 544/283, 284
See application file for complete search history.

(56) References Cited

U.S. PATENT DOCUMENTS

| | | | |
|---|---|---|---|
| 6,391,874 B1 | 5/2002 | Cockerill et al. | |
| 6,713,485 B2 | 3/2004 | Carter et al. | |
| 6,727,256 B1 | 4/2004 | Carter et al. | |
| 6,828,320 B2 | 12/2004 | Cockerill et al. | |
| 7,157,466 B2 | 1/2007 | McClure et al. | |
| 7,651,687 B2 | 1/2010 | Buck et al. | |
| 8,153,643 B2 | 4/2012 | Ple et al. | |
| 8,252,749 B2 | 8/2012 | Steinberg et al. | |
| 8,440,830 B2* | 5/2013 | Maier et al. | 546/113 |
| 2007/0254883 A1 | 11/2007 | Crew et al. | |
| 2008/0051422 A1 | 2/2008 | Tung | |
| 2009/0041767 A1* | 2/2009 | Ramakrishnan et al. | 424/133.1 |
| 2009/0215802 A1 | 8/2009 | Czarnik | |
| 2010/0022093 A1* | 1/2010 | Yamaguchi | 438/706 |
| 2010/0143459 A1 | 6/2010 | Liepold et al. | |
| 2010/0190957 A1 | 7/2010 | Krueger et al. | |
| 2010/0196511 A1 | 8/2010 | Hitoshi et al. | |
| 2010/0311742 A1* | 12/2010 | Mensa-Wilmot | 514/234.5 |
| 2011/0053964 A1 | 3/2011 | Tung et al. | |
| 2011/0097320 A1 | 4/2011 | Tung | |
| 2011/0229406 A1 | 9/2011 | Hettmann et al. | |
| 2011/0263852 A1 | 10/2011 | Jyothi Prasad et al. | |
| 2012/0156200 A1 | 6/2012 | Bing et al. | |
| 2012/0156228 A1 | 6/2012 | Steinberg et al. | |
| 2012/0165351 A1 | 6/2012 | Ple et al. | |

FOREIGN PATENT DOCUMENTS

| | | |
|---|---|---|
| CA | 2 476 008 | 10/2003 |
| CN | 1134438 C | 1/2004 |
| CN | 1305872 C | 3/2007 |
| EP | 0 837 063 | 4/1998 |
| WO | 96/33977 | 10/1996 |
| WO | 97/30035 | 8/1997 |
| WO | WO 98/02434 A1 | 1/1998 |
| WO | 98/13354 | 4/1998 |
| WO | 00/55141 | 9/2000 |
| WO | 01/04111 | 1/2001 |
| WO | 02/41882 | 5/2002 |

(Continued)

OTHER PUBLICATIONS

Vippagunta et al (2000).*
Pinedo et al (2001).*
McMahon et al (2001).*
L. Sun, et al., "Inhibition of tumor angiogenesis by synthetic receptor tyrosine kinase inhibitors," Drug Discov. Today 5(8): 344-353 (2000).
D. Fabbro, et al., "Protein tyrosine kinase inhibitors: new treatment modalities?," Curr. Opin. Pharmacol. 2: 374-381 (2002)
D. Robinson, et al., "The protein tyrosine kinase family of the human genome," Oncogene 19: 5548-5557 (2000).

(Continued)

Primary Examiner — Paul V. Ward

(57) ABSTRACT

The present invention relates to 4-(substituted anilino)-quinazoline derivatives as tyrosine kinase inhibitors. Specifically, compounds of formula I, or pharmaceutically acceptable salts or solvates thereof are disclosed, in which each substitutent in formula I is defined in the description. Preparation method of the compounds of formula I, pharmaceutical compositions and pharmaceutical uses thereof are also disclosed. The compounds of formula I are effective tyrosine kinase inhibitors.

15 Claims, No Drawings

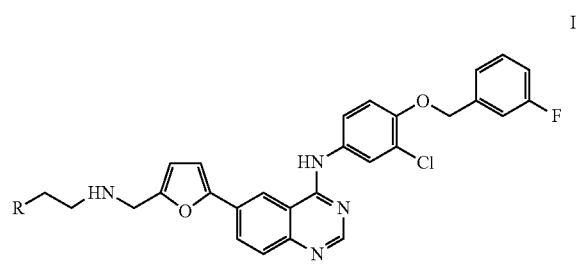

(56) References Cited

FOREIGN PATENT DOCUMENTS

| WO | 03/082290 | 10/2003 |
|---|---|---|
| WO | WO 2004/004644 A2 | 1/2004 |
| WO | WO 2004/004644 A3 | 5/2004 |
| WO | WO 2007/095038 A2 | 8/2007 |
| WO | WO 2007/095038 A8 | 4/2008 |
| WO | 2008/154469 | 12/2008 |
| WO | WO 2009/012647 A1 | 1/2009 |
| WO | WO 2010/017387 A2 | 2/2010 |
| WO | WO 2010/017387 A3 | 5/2010 |
| WO | WO 2011/002523 A1 | 1/2011 |
| WO | WO 2011/035540 A1 | 3/2011 |
| WO | WO 2011/039759 A1 | 4/2011 |
| WO | WO 2011/116634 A1 | 9/2011 |
| WO | WO 2011/130831 A1 | 10/2011 |
| WO | WO 2011/153553 A2 | 12/2011 |
| WO | WO 2012/010088 A1 | 1/2012 |
| WO | WO 2012/010091 A1 | 1/2012 |
| WO | WO 2012/017448 A2 | 2/2012 |
| WO | WO 2012/021830 A1 | 2/2012 |
| WO | WO 2011/153553 A3 | 3/2012 |
| WO | WO 2012/017448 A3 | 5/2012 |
| WO | WO 2012/065935 A1 | 5/2012 |
| WO | WO 2012/089137 A1 | 7/2012 |

OTHER PUBLICATIONS

A. Ullrich, et al., "Signal transduction by receptors with tyrosine kinase activity," Cell 61: 203-212 (1990).

X. Zhu, et al., Acta Pharmaceutica Sinica 37(3): 229-234 (2002).

X. Deng, et al., Actqa Pharmaceutica Sinica 42(12): 1232-1236 (2007).

C. Liebmann, et al., "Regulation of MAP kinase activity by peptide receptor signalling pathway: paradigms of multiplicity," Cellular Signalling 13: 777-785 (2001).

R. Shaw, et al., "Ras, PI(3)K and mTor signalling controls tumour cell growth," Nature 441: 424-430 (2006).

J. Brabender, et al., "Epidermal growth factor receptor and Her-2-neu mRNA Expression in non-small cell lung cancer is correlated with survival," Clin. Cancer Res. 7: 1850-1855 (2001).

J. Martin-Subero, et al., "Amplification of ERBB2, RARA, and TOP2A genes in a myelodysplastic syndrome transforming to acute myeloid leukemia," Cancer Genetics and Cytogenetics 127: 174-176 (2001).

Kapitanovic, et al., "The expression of $p185^{Her-2/neu}$ correlates with the stage of disease and survival in colorectal cancer," Gastroenterology 112: 1103-1113 (1997).

J. Ross, et al., "The Her-2/neu oncogene in tumors of the gastrointestinal tract," Cancer Investigation 19(5): 554-568 (2001).

J. Klijn, et al., "The prognostic value of epidermal growth factor receptor (GFf-R) in primary breast cancer: result for a 10 year follow-up study," Breast Cancer Research and Treatment 29: 73-83 (1994).

H. Scher, "Her2 in prostate cancer—a viable target or innocent bystander," J. Natl. Cancer. Inst. 92(23): 1866-1868 (2000).

I. Hellström, et al., "Overexpression of Her-2 in ovarian carcinomas," Cancer Research 61: 2420-2423 (2001).

H. Shiga, et al., "Prognostic value of c-erbB2 and other markers in patients treated with chemotherapy for recurrent head and neck cancer," Head & Neck 22: 599-608 (2000).

J. Mendelsohn, et al., "The EGF receptor family as targets for cancer therapy," Oncogene 19: 6550-6565 (2000).

K. Petrov., et al., "Optimization and SAR for dual ErbB-1/ErbB-2 tyrosine kinase inhibition in the 6-furanylquinazoline series," Bioorg. Med. Chem. Lett. 16: 4686-4691(2006).

S. Berge, et al., "Pharmaceutical salts," J. Pharmaceutical Sciences 66: 1 (1977).

"Methods in cell biology," Prescott, Ed., vol. XIV, Academic Press, New York, N.Y., p. 33 (1976).

D. Rusnak, et al., "Assessment of epidermal growth factor receptor (EGFR, ErbB1) and HER2 (ErbB2) protein expression levels and response to lapatinib (Tykerb®, GW572016) in an expanded panel of human normal and tumour cell lines," Cell Prolif. 40: 580-594 (2007).

European search report and search opinion dated Jan. 30, 2013 for EP Application No. 10818234.6.

International search report and written opinion dated Dec. 30, 2010 for PCT Application No. CN2010/001449.

International Search Report, issued in corresponding International Application No. PCT/CN2010/001449, (Sep. 20, 2010).

Arteaga, C.L. Epidermal growth factor receptor dependence in human tumors: more than just expression? Oncologist. 2002;7 Suppl 4:31-9.

Barthelemy, et al. Pertuzumab: development beyond breast cancer. Anticancer Res. Apr. 2014;34(4):1483-91.

Esnaola, et al. Phase 2 trial of induction gemcitabine, oxaliplatin, and cetuximab followed by selective capecitabine-based chemoradiation in patients with borderline resectable or unresectable locally advanced pancreatic cancer. Int J Radiat Oncol Biol Phys. Mar. 15, 2014;88(4):837-44. doi: 10.1016/j.ijrobp.2013.12.030.

Frederick, et al. Diversity and frequency of epidermal growth factor receptor mutations in human glioblastomas. Cancer Res. Mar. 1, 2000;60(5):1383-7.

Fujii, M. Recent multidisciplinary approach with molecular targeted drugs for advanced head and neck cancer. Int J Clin Oncol. Apr. 2014;19(2):220-9. doi: 10.1007/s10147-014-0671-9. Epub Feb. 28, 2014.

Hynes, et al. ERBB receptors and cancer: the complexity of targeted inhibitors. Nat Rev Cancer. May 2005;5(5):341-54.

Iwamoto, et al. Multicenter phase II study of second-line cetuximab plus folinic acid/5-fluorouracil/irinotecan (FOLFIRI) in KRAS wild-type metastatic colorectal cancer: the FLIER study. Anticancer Res. Apr. 2014;34(4):1967-73.

Jhaveri, et al. A phase I dose-escalation trial of trastuzumab and alvespimycin hydrochloride (KOS-1022; 17 DMAG) in the treatment of advanced solid tumors. Clin Cancer Res. Sep. 15, 2012;18(18):5090-8. doi: 10.1158/1078-0432.CCR-11-3200. Epub Jul. 10, 2012.

Kurokawa, et al. Phase II study of trastuzumab in combination with S-1 plus cisplatin in HER2-positive gastric cancer (HERBIS-1). Br J Cancer. Mar. 4, 2014;110(5):1163-8. doi: 10.1038/bjc.2014.18. Epub Jan. 28, 2014.

Murphy, et al. Erlotinib or gefitinib for the treatment of relapsed platinum pretreated non-small cell lung cancer and ovarian cancer: a systematic review. Drug Resist Updat. Jun. 2011;14(3):177-90. doi: 10.1016/j.drup.2011.02.004. Epub Mar. 24, 2011.

Nechushtan, et al. A phase 1/2 of a combination of Cetuximab and Taxane for "triple negative" breast cancer patients. Breast. Aug. 2014;23(4):435-8. doi: 10.1016/j.breast.2014.03.003. Epub May 14, 2014.

Okines, et al. Targeting the human EGFR family in esophagogastric cancer. Nat Rev Clin Oncol. Apr. 5, 2011;8(8):492-503. doi: 10.1038/nrclinonc.2011.45.

Pautier, et al. Phase II study of gefitinib in combination with paclitaxel (P) and carboplatin (C) as second-line therapy for ovarian, tubal or peritoneal adenocarcinoma (1839IL/0074). Gynecol Oncol. Feb. 2010;116(2):157-62. doi: 10.1016/j.ygyno.2009.10.076.

Posadas, et al. A phase II and pharmacodynamic study of gefitinib in patients with refractory or recurrent epithelial ovarian cancer. Cancer. Apr. 1, 2007;109(7):1323-30.

Riely, et al. Update on epidermal growth factor receptor mutations in non-small cell lung cancer. Clin Cancer Res. Dec. 15, 2006;12(24):7232-41.

Salomon, et al. Epidermal growth factor-related peptides and their receptors in human malignancies. Crit Rev Oncol Hematol. Jul. 1995;19(3):183-232.

Slamon, et al. Studies of the HER-2/neu proto-oncogene in human breast and ovarian cancer. Science. May 12, 1989;244(4905):707-12.

Tuefferd, et al. HER2 status in ovarian carcinomas: a multicenter GINECO study of 320 patients. PLoS One. Nov. 7, 2007;2(11):e1138.

Wainberg, et al. Phase II trial of modified FOLFOX6 and erlotinib in patients with metastatic or advanced adenocarcinoma of the oesophagus and gastro-oesophageal junction. Br J Cancer. Sep. 6, 2011;105(6):760-5. doi: 10.1038/bjc.2011.280. Epub Aug. 2, 2011.

* cited by examiner

4-(SUBSTITUTED ANILINO)-QUINAZOLINE DERIVATIVES USEFUL AS TYROSINE KINASE INHIBITORS

FIELD OF THE INVENTION

The present invention belongs to the field of medicinal chemistry, and specifically relates to a new class of 4-(substituted anilino)-quinazoline derivatives having an antitumor activity and a process for preparing the same, as well as use of the 4-(substituted anilino)-quinazoline derivatives as a medicament for the treatment or adjuvant treatment of tumors mediated by receptor tyrosine kinases or proliferation and migration of tumor cells driven by receptor tyrosine kinases in a mammal (including a human being).

BACKGROUND OF THE INVENTION

Tumors are one of main diseases that seriously threaten the lives and quality of life of human beings. According to statistical data of the World Health Organization (WHO), patients that die of tumors are about 6.9 millions per year in the world. Since living environment and living habit vary, the morbidity rate and mortality rate of tumors has increased gradually in recent years due to unhealthy environment and some disadvantageous factors.

The traditional treatment regimes for tumors are performed by discovering and destroying tumors. At present, owing to the further research of cell signal transduction pathways and deep knowledge of actions of oncogenes and antioncogenes in tumor cells, the development of antitumor drugs that are directed against cancer-specific molecule targets attracts more attention and becomes a research focus in the art. As a new treatment regime targeted therapy of tumors has been clinically applied, and has got remarkable progress in recent years. It is known that signal pathway of protein tyrosine kinases (PTK) is closely related to the proliferation, differentiation, migration and apoptosis of tumor cells (cf. Li Sun, et al., Drug Discov Today, 2000, 5, 344-353), and a protein tyrosine kinase inhibitor can be used to interfere or block tyrosine kinase pathways to treat tumors (cf. Fabbro D., et al., Curr Opin Pharmacol, 2002, 2, 374-381).

Protein tyrosine kinases (PTK) are members of oncoprotein and proto-oncoprotein families that are important in the normal and abnormal cell proliferation, and are enzymes that can selectively phosphorylate tyrosine residues of different substrates, catalyze the transfer of the γ-phosphate group from adenosine triphosphate to tyrosine residues of many important proteins, and phosphorylate phenolic hydroxyl. Protein tyrosine kinases include receptor tyrosine kinases (RTK), non-receptor tyrosine kinases, and IR and Janus kinases etc. (cf. Robinson D. R., et al., Oncogene, 2000, 19, 5548-5557), wherein most of them are receptor tyrosine kinases (RTK). Receptor tyrosine kinases (RTK) are endogenous protein tyrosine kinases, take part in the regulation of a number of cells, play an important role in the transmission of mitogenic signals which initiate cell replication, and regulate the cell growth and differentiation. All RTKs belong to type I membrane-spanning cell surface proteins having a similar topological structure, i.e., they have a large glycosylated extraceullular ligand binding domain, a hydrophobic transmembrane domain, and an intracellular tyrosine kinase catalytic domain as well as a regulation sequence. It is known that ligand binding (for example, the binding of an epidermal growth factor (EGF) or of an EGFR) results in activation of activity of partially encoded receptor kinase in the receptor, thereby phosphorylating critical tyrosine amino acids to lead to transduction of proliferative signal across cell membrane.

The receptor tyrosine kinases can be divided into 4 different sub-groups based on the different structures of subunits in the extraceullular ligand binding domain (cf. Ullrich A. et al., Cell, 1990, 61, 203-212): the first sub-group (i.e., erbB family) comprises epidermal growth factor receptor (EGFR), HER2/Neu, HER3/c-erbB3, and the like; the second sub-group comprises insulin receptors, insulin-like growth factor-1 (IGF-1) receptors, and the like; the third sub-group comprises PDGFR-α, PDGFR-β, colony-stimulating actor-1 receptors (CSF-IR), c-Kit, and the like; and the further sub-group comprises FGFR-1, FGFR-2, FGFR-3, FGFR-4, and the like, wherein the third and fourth sub-groupes contain 5 and 3 extracellular immunoglobulin-like domains, respectively. After binding to a corresponding ligand, RTK can initiate the formation of a homodimer or heterodimer in receptors, activate PTK, and catalyze the transfer of the phosphate group from adenosine triphosphate to tyrosine residues of receptors to phosphorylate the tyrosine residues. The autophosphorylation of receptors produces two effects, that is, activation of inherent catalytic activity and formation of binding sites of effect proteins, to thereby activate downstream signal molecules (cf. Zhu Xiaofeng et al, Acta Pharmaceutica Sinica, 2002, 37, 229-234; Deng Xiaoqiang et al, Acta Pharmaceutica Sinica, 2007, 42, 1232-1236).

Main signal transduction pathways of the receptor tyrosine kinases include Ras (retrovirus-associated DNA sequences)/Raf (rapidly accelerated fibrosarcoma)/MAPK (mitogen activated protein kinase) pathways and PI-3K (phosphatidylinositol-3 kinase)/Akt (protein kinase B, PKB) pathways. Ras/Raf/MAPK pathways primarily regulate cell proliferation and survival. MAPK is a mitogenic signal, and an activated MAPK enters into cell nucleus and activates transcription factors (e.g. Elkl, Etsl, c-Myc, and the like) due to phosphorylation, thereby interfering cell cycle and transformation process, resulting in the formation of tumors. MAPKs also can induce degradation of proteins and substrates, promote cell migration, and maintain tumor growth (cf. Liebmann C., et al., Cell Signal, 2001, 13, 777-785). PI-3K/Akt signal transduction pathways involve cell growth, apoptosis inhibition, invasion, and migration processes, and play an important role same as that of Ras/Raf/MAPK pathways, wherein, Akt transfers into cell nucleus and regulate more transcription factors (e.g., FKHRL1, NF-$_\kappa$B, Bcl-2, and the like) due to phosphorylation, thereby inhibiting the expression of apoptotic genes; Akt also can phosphorylate glycogen synthase kinase-3 (GSK-3) and mammalian target of rapamycin (mTOR), and hence to upregulate Cyclin D, and phosphorylate a series of inhibitory proteins (e.g., $21^{CIPI}$ and $p27^{KIPI}$), and lead to a shorten cell cycle, resulting in tumorigenesis (cf. Shaw R. J., et al., Nature, 2006, 441, 424-430). Therefore, the phosphorylation of receptors catalyzed by PTK ultimately promotes cell proliferation, inhibits cell apoptosis, which is directly associated with tumorigenesis.

The known research results have showed that the receptor tyrosine kinases such as Bcr-abl, EGFR, HER and the like are overexpressed in patients suffering from tumors, in particular, the overexpression of the erbB family (e.g., EFGR, HER2, and the like) can be detected in many human cancers, such as non-small cell lung cancer (NSCLC) (cf. Brabender J., et al., Clin Cancer Res, 2001, 7, 1850-1855), leukemia (cf. Jose Ignacio Martin-Suberoac, et al., Cancer Genet Cytogenet, 2001, 127, 174-176), gastrointestinal cancer (cf. Kapitanovic S., et al., Gastroenterology, 2000, 112, 1103-1113; Ross J. S., et al., Cancer Invest, 2001, 19, 554-558), breast cancer (cf. Klijn J. S., et al., Breast Cancer Res Treat, 1994, 29, 73-83), prostatic cancer (cf. Scher H. I., et al., J Natl Cancer Inst, 2000, 92, 1866-1868), ovarian cancer (cf. Hellstrom I., et al., Cancer Res, 2001, 61, 2420-2423), head and neck cancer (cf. Shiga H., et al., Head Neck, 2000, 22, 599-608), and the like. As the expression of receptor tyrosine kinases in more human tumor tissues and relationship between PTK signal pathways and tumors are further deeply researched, this kind of target sites necessarily produce innovations in the treatment regimes for tumors.

There are abnormal signal transduction pathways in a number of tumor cells, for example, the overexpression of the EGFR proteins are usually seen in epidermal cell derived tumors, the overexpression of PDEFR proteins are usually seen in glioma, and overactivation of Bcr-Abl in CML, and the like. As the results wrong regulations of one or more receptors, multiple tumors clinically become more invasive, and thus are closely related to bad prognosis (cf. Ross J. S., et al., Cancer Investigation, 2001, 19, 554-568). In addition to the aforesaid clinical discoveries, many clinical researches demonstrate that the tyrosine kinases in the erbB family are associated with cytometaplasia, that is, one or more erbB receptors are overexpressed in many cell lines, and EFGR or erbB2 proteins are able to transform non-tumor cells when transfected into these cells. Moreover, many preclinical studies show that the activity of one or more erbB receptors is eliminated by using small molecular inhibitors or inhibitory antibodies to induce effect against proliferation (cf. Mendelsohn J., et al., Oncogene, 2000, 19, 6550-6565).

In recent years, it has been focused on inhibition of the cell signal transduction pathways to develop novel targeted anti-tumor drugs. Singal transduction inhibitors promote cell apoptosis by downregulation of survival and proliferative signals of tumors rather than by cytotoxicity, so that the selectivity is high and toxic side effect is low. At present, there are dozens of signal transduction inhibitors that are clinically applied to treat tumors, and they are mainly tyrosine kinase inhibitors as antitumor drugs, for example, the development of compounds having a structure of 4-(substituted anilino)-quinazoline is advanced for small molecular inhibitors directed against target sites of EGFR tyrosine kinases, such as Gefitinib (Iressa), Erlotinib (Tarceva), Lapatinib, and the like.

Gefitinib is an EGFR tyrosine kinase inhibitor developed by AstraZeneca with a trade name of Iressa, the first EGFR tyrosine kinase inhibitor that is clinically investigated and marketed in Japan in 2002 and in U.S. 2003, and is indicated for the treatment of patients with advanced or metastatic non-small cell lung cancer (NSCLC) who have received prior chemotherapies. Erlotinib is an EGFR tyrosine kinase inhibitor developed by OSI with a trade name of Tarceva, transferred to Genentech and Roche, marketed in America in 2004, and is indicated for the treatment of NSCLC and pancreatic cancer. Erlotinib belongs to the first generation of anilino-quinazoline small molecule inhibitors for the treatment of NSCLC, and is a unique EGFR tyrosine kinase inhibitor that has been confirmed to exhibit survival advantage for advanced NSCLC. Erlotinib is effective for various NSCLC, has a good tolerance, exhibits no myelosuppression and cytotoxicity, and can significantly extends survival and improve quality of life of patients. Lapatinib (with its trade name of Tycerb) is a dual inhibitor of EGFR and HER2 developed by GlaxoSmithKline, and exhibits an inhibitory activity against signal transduction of tumor proliferation and survival higher than a signal receptor inhibitor. Lapatinib was approved by the Food and Drug Administration of America in 2007, and indicated in combination with capecitabine for the treatment of advanced or metastatic breast cancer with overexpression of HER2 and subjected to chemotherapy of such as anthracyclines, taxanes and trastuzumab.

In addition, the published patent applications WO 96/33977, WO 97/30035, WO 98/13354, WO 00/55141, WO 02/41882, WO 03/82290 and EP 837063, all disclose certain quinazoline derivatives substituted with anilino group at 4-position or substituent(s) at 6- and/or 7-position have the inhibitory activity of receptor tyrosine kinases.

Small molecule tyrosine kinase inhibitors as new targeting anticancer drugs open novel window for the treatment and prevention of tumors, and they have slight side effects and good tolerance. Although dozens of small molecule tyrosine kinase inhibitors have made a significant contribution to the clinical treatment of tumors, there is needed to discover additional compounds having better in vivo activity and/or improved pharmacological action than the current tyrosine kinase inhibitors. Therefore, it is of very important significance for the clinical treatment of tumors to develop novel and improved or more effective tyrosine kinase inhibitors, and to deeply investigate the relationship between such new inhibitors and the known target proteins as well as the mechanism of action thereof.

DESCRIPTIONS OF THE INVENTION

An object of the present invention is to discover novel compounds having an effective inhibition on tyrosine kinases. The present inventors have surprisingly found that 4-(substituted anilino)-quinazoline derivatives of formula I have an effective inhibition on tyrosine kinases and/or good pharmacokinetics in vivo. The present invention is accomplished on the basis of the discovery.

Therefore, the first aspect of the present invention provides a compound of formula I, or pharmaceutically acceptable salts or solvates thereof,

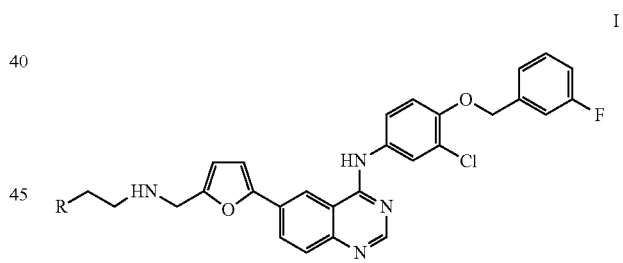

wherein:
R is selected from a $C_{1-6}$-alkylsulfinyl, a $C_{1-6}$-alkylsulfinyl substituted with one or more halogens, a $C_{1-6}$-alkylthio, a $C_{1-6}$-alkylthio substituted with one or more halogens, a $C_{1-6}$-alkylamido, a $C_{1-6}$-alkylsulfonamido, a $C_{1-6}$-alkylsulfonamido substituted with one or more halogens, a $C_{1-6}$-alkylsulfonyl substituted with one or more halogens, or a group of formula

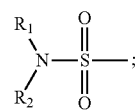

wherein $R_1$ and $R_2$ each are independently selected from the group consisting of hydrogen, a $C_{1-6}$-alkyl, and a $C_{1-6}$-alkyl substituted with one or more halogens.

According to an embodiment of the first aspect, the present invention provides the compound of formula I, wherein R is selected from a $C_{1-6}$-alkylsulfinyl, a $C_{1-6}$-alkylsulfinyl substituted with one or more halogens. In one embodiment of a compound of formula I of the present invention, R is selected from a $C_{1-4}$-alkylsulfinyl, or a $C_{1-4}$-alkylsulfinyl substituted with 1 to 3 halogens.

According to an embodiment of the first aspect, the present invention provides the compound of formula I, wherein R is selected from a $C_{1-6}$-alkylthio, a $C_{1-6}$-alkylthio substituted with one or more halogens. In one embodiment of a compound of formula I of the present invention, R is selected $C_{1-4}$-alkylthio, or a $C_{1-4}$-alkylthio substituted with 1 to 3 halogens.

According to an embodiment of the first aspect, the present invention provides the compound of formula I, wherein R is selected from a $C_{1-6}$-alkylamido, a $C_{1-6}$-alkylsulfonamido, or a $C_{1-6}$-alkylsulfonamido substituted with one or more halogens. In one embodiment of a compound of formula I of the present invention, R is selected from a $C_{1-4}$-alkylamido, a $C_{1-4}$-alkylsulfonamido, or a $C_{1-4}$-alkylsulfonamido substituted with 1 to 3 halogens.

According to an embodiment of the first aspect, the present invention provides the compound of formula I, wherein R is selected from a $C_{1-6}$-alkylsulfonyl substituted with one or more halogens. In one embodiment of a compound of formula I of the present invention, R is selected from a $C_{1-4}$-alkylsulfonyl substituted with 1 to 3 halogens.

According to an embodiment of the first aspect, the present invention provides the compound of formula I, wherein R is selected from a group of formula

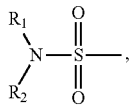

wherein $R_1$ and $R_2$ have the meanings as defined for the compound of formula I according to the first aspect of the present invention. In one embodiment of a compound of formula I of the present invention, R is selected from a group of formula

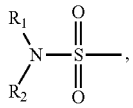

wherein $R_1$ and $R_2$ each are independently selected from the group consisting of hydrogen, a $C_{1-4}$-alkyl, and a $C_{1-4}$-alkyl substituted with 1 to 3 halogens, such as hydrogen, methyl, ethyl, and trifluoromethyl.

According to an embodiment of the first aspect, the present invention provides the compound of formula I, wherein R is selected from a $C_{1-4}$-alkylsulfinyl, a $C_{1-4}$-alkylsulfinyl substituted with 1 to 3 halogens, a $C_{1-4}$-alkylthio, a $C_{1-6}$-alkylthio substituted with 1 to 3 halogens, a $C_{1-4}$-alkylamido, a $C_{1-4}$-alkylsulfonamido, a $C_{1-4}$-alkylsulfonamido substituted with 1 to 3 halogens, a $C_{1-4}$-alkylsulfonyl substituted with 1 to 3 halogens, or a group of formula

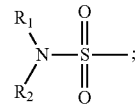

wherein $R_1$ and $R_2$ each are independently selected from the group consisting of hydrogen, a $C_{1-4}$-alkyl, and a $C_{1-4}$-alkyl substituted with 1 to 3 halogens.

According to an embodiment of the first aspect, the present invention provides the compound of formula I, wherein said halogen is selected from fluorine, chlorine or bromine. In one embodiment, said halogen is selected from fluorine or chlorine, preferably fluorine.

According to an embodiment of the first aspect, the present invention provides the compound of formula I, wherein said alkyl is a linear or branched alkyl group.

According to an embodiment of the first aspect, the present invention provides the compound of formula I, wherein said alkyl is selected from the group consisting of methyl, ethyl, n-propyl, iso-propyl, n-butyl, sec-butyl, tert-butyl, pentyl, and hexyl. In one embodiment, said alkyl is selected from the group consisting of methyl, ethyl, n-propyl, iso-propyl, n-butyl, sec-butyl, and tert-butyl. In one embodiment, said alkyl is selected from methyl, ethyl, n-propyl, iso-propyl, and n-butyl.

According to an embodiment of the first aspect, the present invention provides the compound of formula I, wherein said pharmaceutically acceptable salts are selected from the group consisting of hydrochloride, sulfate, mesylate, xylenesulphonate, fumarate, and maleate, or solvates such as hydrates thereof.

According to an embodiment of the first aspect, the present invention provides the compound of formula I, which is selected from the group consisting of:

N-(4-(3-fluorobenzyloxy)-3-chlorophenyl)-6-(5-((2-(sulfamoyl)ethylamino)methyl)-2-furyl)-quinazolin-4-amine;

N-(4-(3-fluorobenzyloxy)-3-chlorophenyl)-6-(5-((2-(methylsulfinyl)ethylamino)methyl)-2-furyl)-quinazolin-4-amine;

N-(4-(3-fluorobenzyloxy)-3-chlorophenyl)-6-(5-((2-(methylthio)ethylamino)methyl)-2-furyl)-quinazolin-4-amine;

N-(4-(3-fluorobenzyloxy)-3-chlorophenyl)-6-(5-((2-(methanesulfonamido)ethylamino)methyl)-2-furyl)-quinazolin-4-amine;

N-(4-(3-fluorobenzyloxy)-3-chlorophenyl)-6-(5-((2-(2,2,2-trifluoro ethylsulfonyl)ethylamino)methyl)-2-furyl)-quinazolin-4-amine;

N-(4-(3-fluorobenzyloxy)-3-chlorophenyl)-6-(5-((2-(trifluoromethylsulfonyl)ethylamino)methyl)-2-furyl)-quinazolin-4-amine;

N-(4-(3-fluorobenzyloxy)-3-chlorophenyl)-6-(5-((2-(trifluoromethylthio)ethylamino)methyl)-2-furyl)-quinazolin-4-amine;

N-(4-(3-fluorobenzyloxy)-3-chlorophenyl)-6-(5-((2-(trifluoromethylsulfinyl)ethylamino)methyl)-2-furyl)-quinazolin-4-amine;

N-(4-(3-fluorobenzyloxy)-3-chlorophenyl)-6-(5-((2-(2,2,2-trifluoroethylthio)ethylamino)methyl)-2-furyl)-quinazolin-4-amine;

N-(4-(3-fluorobenzyloxy)-3-chlorophenyl)-6-(5-((2-(2,2,2-trifluoroethylsulfinyl)ethylamino)methyl)-2-furyl)-quinazolin-4-amine;

N-(4-(3-fluorobenzyloxy)-3-chlorophenyl)-6-(5-((2-(acetamido)ethylamino)methyl)-2-furyl)-quinazolin-4-amine;

N-(4-(3-fluorobenzyloxy)-3-chlorophenyl)-6-(5-((2-(N-methylsulfamoyl)ethylamino)methyl)-2-furyl)-quinazolin-4-amine;

N-(4-(3-fluorobenzyloxy)-3-chlorophenyl)-6-(5-((2-(N-ethylsulfamoyl)ethylamino)methyl)-2-furyl)-quinazolin-4-amine; and N-(4-(3-fluorobenzyloxy)-3-chlorophenyl)-6-(5-((2-(2,2,2-trifluoroethylsulfonamido)ethylamino)methyl)-2-furyl)-quinazolin-4-amine;

or pharmaceutically acceptable salts or solvates thereof.

According to an embodiment of the first aspect, the present invention provides the compound of formula I, which is selected from the group consisting of:

N-(4-(3-fluorobenzyloxy)-3-chlorophenyl)-6-(5-((2-(sulfamoyl)ethylamino)methyl)-2-furyl)-quinazolin-4-amine;

N-(4-(3-fluorobenzyloxy)-3-chlorophenyl)-6-(5-((2-(methylsulfinyl)ethylamino)methyl)-2-furyl)-quinazolin-4-amine;

N-(4-(3-fluorobenzyloxy)-3-chlorophenyl)-6-(5-((2-(methylthio)ethylamino)methyl)-2-furyl)-quinazolin-4-amine;

N-(4-(3-fluorobenzyloxy)-3-chlorophenyl)-6-(5-((2-(methanesulfonamido)ethylamino)methyl)-2-furyl)-quinazolin-4-amine;

N-(4-(3-fluorobenzyloxy)-3-chlorophenyl)-6-(5-((2-(2,2,2-trifluoroethylsulfonyl)ethylamino)methyl)-2-furyl)-quinazolin-4-amine; and N-(4-(3-fluorobenzyloxy)-3-chlorophenyl)-6-(5-((2-(trifluoromethylsulfonyl)ethylamino)methyl)-2-furyl)-quinazolin-4-amine, or pharmaceutically acceptable salts or solvates thereof.

According to an embodiment of the first aspect, the present invention provides the compound of formula I, which is selected from the group consisting of:

N-(4-(3-fluorobenzyloxy)-3-chlorophenyl)-6-(5-((2-(sulfamoyl)ethylamino)methyl)-2-furyl)-quinazolin-4-amine;

N-(4-(3-fluorobenzyloxy)-3-chlorophenyl)-6-(5-((2-(methylsulfinyl)ethylamino)methyl)-2-furyl)-quinazolin-4-amine;

N-(4-(3-fluorobenzyloxy)-3-chlorophenyl)-6-(5-((2-(methylthio)ethylamino)methyl)-2-furyl)-quinazolin-4-amine;

N-(4-(3-fluorobenzyloxy)-3-chlorophenyl)-6-(5-((2-(methanesulfonamido)ethylamino)methyl)-2-furyl)-quinazolin-4-amine; and N-(4-(3-fluorobenzyloxy)-3-chlorophenyl)-6-(5-((2-(2,2,2-trifluoroethylsulfonyl)ethylamino)methyl)-2-furyl)-quinazolin-4-amine, or pharmaceutically acceptable salts or solvates thereof.

The second aspect of the present invention provides a process for preparing a compound of formula I according to an embodiment of the first aspect of the present invention, comprising the following steps:

a) reacting a compound of formula II, or a salt or reactive derivative thereof

II with a compound of formula III or an appropriate salt thereof.

NH$_2$CH$_2$CH$_2$R    III in the presence of a suitable base and in a suitable solvent such as an organic solvent; and b) treating the reaction mixture with a suitable reducing agent to give the compound of formula I, wherein R has the meaning as defined in any embodiment of the first aspect of the present invention.

According to an embodiment of the second aspect, the present invention provides the process for preparing a compound of formula I, wherein the base may be an organic base such as triethylamine, triethanolamine, alkyldimethylamine, and sodium methoxide etc., or an inorganic base such as sodium hydroxide, potassium hydroxide, and sodium carbonate etc. In one embodiment, the base is triethylamine.

According to an embodiment of the second aspect, the present invention provides the process for preparing a compound of formula I, wherein the salt of a compound of formula III is selected from the group consisting of hydrochloride, sulfate, and nitrate, or the like. In one embodiment, the salt of a compound of formula III is a hydrochloride salt.

According to an embodiment of the second aspect, the present invention provides the process for preparing a compound of formula I, wherein the reducing agent is selected from the group consisting of sodium borohydride, sodium cyanoborohydride, and sodium triacetoxyborohydride, and the like. In one embodiment, the reducing agent is sodium borohydride. In another embodiment, the reducing agent is sodium cyanoborohydride.

According to an embodiment of the second aspect, the present invention provides the process for preparing a compound of formula I, wherein any functional groups in formula II and H$_2$CH$_2$CH$_2$R are protected, if desirable.

In the process according to the second aspect of the present invention, if necessary, some groups (e.g., amino, hydroxyl groups etc.) are required to be protected during the preparation of a compound of formula I to prevent undesirable reactions, and in the meantime, protecting groups are deprotected when appropriate. Such examples are too numerous to mention, and the use of protecting groups and deprotecting methods which are not specifically mentioned all are within the scope of the present invention.

In the process according to the second aspect of the present invention, the compounds of formula II can be prepared by a person skilled in the art according to known techniques in the art, and in one exemplary method, the compounds of formula II can be prepared according to the reference documents, for example, Kimberly G. Petrov, et al., Bioorg. Med. Chem. Lett., 2006, 16: 4686-4691.

The third aspect of the present invention relates to a pharmaceutical composition comprising a compound of formula I according to any embodiment of the first aspect of the present invention, and optionally one or more pharmaceutically acceptable carrier(s) or excipient(s).

The fourth aspect of the present invention relates to use of a compound of formula I according to any embodiment of the first aspect of the present invention in the manufacture of a medicament for the treatment and/or prophylaxis of a disease or disorder associated with receptor tyrosine kinases in a mammal (including a human being).

The fourth aspect of the present invention also relates to the use of a compound of formula I according to any embodiment of the first aspect of the present invention in the manufacture of a medicament for the treatment or adjuvant treatment and/or prophylaxis of a receptor tyrosine kinase-medicated tumor or receptor tyrosine kinase-driven proliferation and migration of tumor cells in a mammal (including a human being).

It can be completely predicted according to the present invention that the compounds of the present invention can be used to treat cancers susceptible to erbB receptor tyrosine kinase, for example, tumors in which EGFR or Her2 are overexpressed and EGF-driven tumors, including solid tumors, such as, cancers of bile duct, bone, bladder, brain/central nervous system, breast, colorectal intestine, endometrium, stomach, head and neck, liver, lung (especially non-small cell lung cancer), neuron, esophagus, ovary, pancreas, prostate, kidney, skin, testis, thyroid gland, uterus, vulva, and the like, and non-solid tumors, such as leukemia, multiple myeloma, or lymphoma, and the like. Therefore, the tumors or cancers involved in the above terms "a disease or disorder associated with receptor tyrosine kinases" and "a receptor tyrosine kinase-medicated tumor" or "receptor tyrosine kinase-driven proliferation and migration of tumor cells" may include the cancers susceptible to erbB receptor tyrosine kinase, for example, tumors in which EGFR or Her2 are overexpressed and EGF-driven tumors, including solid tumors, such as, cancers of bile duct, bone, bladder, brain/central nervous system, breast, colorectal intestine, endometrium, stomach, head and neck, liver, lung (especially non-small cell lung cancer), neuron, esophagus, ovary, pancreas, prostate, kidney, skin, testis, thyroid gland, uterus, vulva, and the like, and non-solid tumors, such as leukemia, multiple myeloma, or lymphoma, and the like.

The fifth aspect of the present invention relates to a method for the treatment and/or prophylaxis of a disease or disorder associated with receptor tyrosine kinases in a mammal in need thereof, comprising administering the mammal in need thereof a therapeutically effective amount of a compound of formula I according to any embodiment of the first aspect of the present invention.

The fifth aspect of the present invention also relates to a method for the treatment or adjuvant treatment and/or prophylaxis of a receptor tyrosine kinase-medicated tumor or receptor tyrosine kinase-driven proliferation and migration of tumor cells in a mammal (including a human being) in need thereof, comprising administering the mammal in need thereof a therapeutically effective amount of a compound of formula I according to any embodiment of the first aspect of the present invention.

The fifth aspect of the present invention further relates to a method for the treatment and/or prophylaxis of a tumor or cancer in a mammal (including a human being) in need thereof, comprising administering the mammal in need thereof a therapeutically effective amount of a compound of formula I according to any embodiment of the first aspect of the present invention, wherein said tumors or cancers include the cancers susceptible to erbB receptor tyrosine kinase, for example, tumors in which EGFR or Her2 are overexpressed and EGF-driven tumors, including solid tumors, such as, cancers of bile duct, bone, bladder, brain/central nervous system, breast, colorectal intestine, endometrium, stomach, head and neck, liver, lung (especially non-small cell lung cancer), neuron, esophagus, ovary, pancreas, prostate, kidney, skin, testis, thyroid gland, uterus, vulva, and the like, and non-solid tumors, such as leukemia, multiple myeloma, or lymphoma, and the like.

The sixth aspect of the present invention relates to a pharmaceutical composition for the treatment and/or prophylaxis of a disease or disorder associated with receptor tyrosine kinases, which pharmaceutical composition comprises a compound of formula I according to any embodiment of the first aspect of the present invention, and optionally one or more pharmaceutically acceptable carrier(s) or excipient(s).

The sixth aspect of the present invention also relates to a pharmaceutical composition for the treatment or adjuvant treatment and/or prophylaxis of a receptor tyrosine kinase-medicated tumor or receptor tyrosine kinase-driven proliferation and migration of tumor cells in a mammal (including a human being), which pharmaceutical composition comprises a compound of formula I according to any embodiment of the first aspect of the present invention, and optionally one or more pharmaceutically acceptable carrier(s) or excipient(s).

The sixth aspect of the present invention further relates to a pharmaceutical composition for the treatment and/or prophylaxis tumor or cancer in a mammal (including a human being), which pharmaceutical composition comprises a compound of formula I according to any embodiment of the first aspect of the present invention, and optionally one or more pharmaceutically acceptable carrier(s) or excipient(s), wherein the said tumors or cancers include the cancers susceptible to erbB receptor tyrosine kinase, for example, tumors in which EGFR or Her2 are overexpressed and EGF-driven tumors, including solid tumors, such as, cancers of bile duct, bone, bladder, brain/central nervous system, breast, colorectal intestine, endometrium, stomach, head and neck, liver, lung (especially non-small cell lung cancer), neuron, esophagus, ovary, pancreas, prostate, kidney, skin, testis, thyroid gland, uterus, vulva, and the like, and non-solid tumors, such as leukemia, multiple myeloma, or lymphoma, and the like.

The seventh aspect of the present invention relates to a compound of formula I according to any embodiment of the first aspect of the present invention for the treatment and/or prophylaxis of a disease or disorder associated with receptor tyrosine kinases.

The seventh aspect of the present invention also relates to a compound of formula I according to any embodiment of the first aspect of the present invention for the treatment or adjuvant treatment and/or prophylaxis of a receptor tyrosine kinase-medicated tumor or receptor tyrosine kinase-driven proliferation and migration of tumor cells in a mammal (including a human being).

The seventh aspect of the present invention further relates to a compound of formula I according to any embodiment of the first aspect of the present invention for the treatment and/or prophylaxis tumor or cancer in a mammal (including a human being), wherein the said tumors or cancers include the cancers susceptible to erbB receptor tyrosine kinase, for example, tumors in which EGFR or Her2 are overexpressed and EGF-driven tumors, including solid tumors, such as, cancers of bile duct, bone, bladder, brain/central nervous system, breast, colorectal intestine, endometrium, stomach, head and neck, liver, lung (especially non-small cell lung cancer), neuron, esophagus, ovary, pancreas, prostate, kidney, skin, testis, thyroid gland, uterus, vulva, and the like, and non-solid tumors, such as leukemia, multiple myeloma, or lymphoma, and the like.

The characteristics in any aspect of the present invention or any embodiment of such any aspect may apply to any other aspect or any embodiment of such any other aspect, provided that they are not contradict each other. Of course, when they are reciprocal, if necessary, the corresponding characteristics may be suitably modified. In the present invention, for example, when the expression "any embodiment of the first aspect of the present invention" is mentioned, the term "any" refers to any subsidiary aspect of the first aspect of the present invention; when a similar expression relating to other aspects is mentioned, this term has same meanings.

The present invention is further described as follows.

All references as cited in the present invention are incorporated herein by reference, and if the meanings expressed in these references are different from those as defined in the present invention, the expressions in the present invention shall prevail. In addition, the terms and phrases used in the present invention have common meanings as well known by those skilled in the art, unless indicated otherwise. Nevertheless, it is desired in the present invention to further illustrate and explain these terms and phrases in more detail. If the mentioned terms and phrases have meanings different from their common meanings, the meanings expressed in the present invention shall prevail.

In the compounds of formula I of the present invention, the quinazoline ring can be numbered according to the following exemplary sequences:

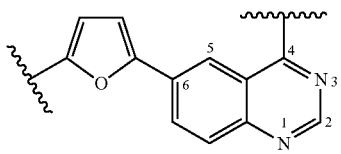 [SMILES: *c1ccc(-c2ccc3ncnc(*)c3c2)o1]

The term "halogen" or "halo" used herein refers to fluorine, chlorine, bromine and iodine.

In the present invention, when mentioned, the used term "hydrocarbyl" includes alkyl, alkenyl and alkynyl.

In the present invention, when mentioned, the used terms "alkyl", "alkenyl" and "alkynyl" have common meanings well known in the art, they are linear or branched hydrocarbyl groups, such as but not limited to methyl, ethyl, propyl, isopropyl, n-butyl, sec-butyl, tert-butyl, allyl, propenyl, propynyl, and the "alkyl", "alkenyl" and "alkynyl" can also be collectively called "hydrocarbyl" or "aliphatic hydrocarbyl".

In the process for synthesizing a compound of formula I of the present invention, all the used raw materials can be prepared according to the prior art, or prepared according to the methods known in the prior art, or commercially available, unless specified otherwise. The intermediates, raw materials, reagents and reaction conditions used in the above reaction scheme all can be modified by those skilled in the art. In addition, those skilled in the art can also synthesized other compounds of formula I not enumerated in the present invention according to the method of the second aspect of the present invention.

The compound of formula I of the present invention can be used in combination with an additional active ingredient, if only the active ingredient does not produce disadvantageous effect, such as anaphylaxis.

The active compound shown in formula I of the present invention can be used as an anticancer drug alone, or in combination with one or more additional antitumor drugs. The combined therapy is carried out by administering each of therapeutic components simultaneously, orderly or separately.

In the present invention, the term "composition" refers to a product comprising the designated amounts of the designated ingredients, and any products directly or indirectly obtained by combining various designated ingredients of designated amounts.

The compounds of the present invention can be used in the forms of pharmaceutically acceptable salts derived from inorganic acids or organic acids. The term "pharmaceutically acceptable salts" refers to the salts that are suitable for contacting with tissues of human beings or lower animals without excessive toxicity, stimulation, anaphylaxis, and the like, and are commensurate to reasonable ratio of effect/risk within the range of reliable medical decisions. The pharmaceutically acceptable salts are well known in the art. For instance, S. M. Berge, et al. describes detailed pharmaceutically acceptable salts (cf. S. M. Berge, et al., J. Pharmaceutical Sciences, 1977, 66: 1). The salts can be in situ prepared in the final separation and purification process of the compounds of the present invention or prepared alone by reaction of the free basic functional groups of the compounds of the present with a suitable organic acid. The typical acid addition salts include but are not limited to acetate, adipate, alginate, citrate, aspartate, benzoate, benzenesulfonate, bisulfate, butyrate, camphorate, camphor sulfonate, digluconate, glycerophosphate, hemisulfate, heptylate, caproate, fumarate, hydrochloride, hydrobromide, hydroiodide, 2-hydroxyesylate (isothionate), lactate, maleate, mesylate, nicotinate, 2-napsylate, oxalate, palmate, pectate, persulfate, 3-phenylpropionate, picrate, pivalate, propionate, succinate, tartrate, thiocyanide, phosphate, glutamate, bicarbonate, p-tosylate and undecanoate. Likewise, alkaline nitrogen-containing group can be quaternized with the following substances: low alkyl halogenides such as chlorides, bromides and iodides of ethyl, propyl and butyl; dialkyl sulfates such as dimethyl sulfate, diethyl sulfate, dibutyl sulfate and dipentyl sulfate; long chain halogenides such as chlorides, bromides and iodides of decyl, dodecyl, tetradecyl and octadecyl; arylalkyl halogenides such as benzyl bromide, phenylethyl bromide and so on. Hence, a product solvable or dispersible in water or oil can be obtained. The examples of acid capable of forming a pharmaceutically acceptable acid addition salt include inorganic acids such as hydrochloric acid, hydrobromic acid, sulfuric acid and phosphoric acid, and organic acids such as oxalic acid, maleic acid, succinic acid and citric acid.

Base addition salts can be in situ prepared in the final separation and purification process of the compounds of the present invention by reacting the free carboxylic acid moiety of the compounds of the present with a suitable base, and the base can be, for example, a pharmaceutically acceptable hydroxides, carbonates and bicarbonates of metal cationic ions, or ammonia or organic primary amines, secondary amines or tertiary amines.

The pharmaceutically acceptable salts include but are not limited to salts based on cationic ions of alkali metals or alkaline earth metals, such as lithium, sodium, potassium, magnesium and aluminum, etc., and non-toxic quaternary ammonium and amine cationic ions, including ammonium, tetramethylammonium, tetraethylammonium, methylammonium, dimethylammonium, trimethylammonium, triethylammonium, diethylammonium, and ethylammonium, etc. The typical organic amines capable of forming the base addition salts include ethylenediamine, ethanolamine, diethanolamine, piperidine, piperazine, etc.

The compounds of formula I of the present invention further comprise isomers, racemics, enantiomers, diastereomers, enantiomers-enriched product, solvates, and esters thereof, and the compounds of formula I of the present invention and isomers, racemics, enantiomers, diastereomers, enantiomers-enriched product, solvates and esters thereof can further form solvates, such as hydrates, alcoholic solvates, etc. The compounds can further be prodrugs or in form of capable of releasing the active ingredient after in vivo metabolism. It is common knowledge for a skilled in the art to select and prepare a suitable prodrug derivative. Generally, for the purpose of the present invention, solvates of the present compounds with pharmaceutically acceptable solvents such as water, ethanol are equivalent to the present compounds in the form of non-solvates.

The actual dose level of various active ingredients in a pharmaceutical composition of the present invention can be varied so that the resultant amount of active compounds can lead to desired therapeutic reactions in specific patients, dosage forms and administration modes. The dose level must be determined according to the activity of specific compound, administration route, severity of disease to be treated, and conditions and past medical history of patients. However, the conventional method in the art is to increase gradually the dose of compound from a level lower than that for achieving desired therapeutic effects to a level enough to achieve the desired therapeutic effects.

In the aforementioned or other treatment and/or prophylaxis, a compound of the present invention in a therapeutically and/or prophylactically effective amount can be used in form of pure compound, or in form of pharmaceutically acceptable esters or prodrugs thereof (if they exist). Alternatively, the compound can be administered via a pharmaceutical composition comprising the compound and one or more pharmaceutically acceptable excipients. The term "therapeutically and/or prophylactically effective amount" of the compound of the present invention means that the compound is in an amount sufficient to achieve prophylactically and/or therapeutically reasonable ratio of effect/risk. It should be understood that the total amount per day of the compound or composition of the present invention must be determined by a physician within the range of reliable medical decisions. As for any specific patients, the specific therapeutically amount must be determined based on various factors, including the diseases to be treated and severity thereof, the activity of the used specific compound, the used specific composition, the age, body weight, general health status, gender and food of patient, the administration time and route and excretory rate of the used specific compound, the drug(s) administered in combination or simultaneously with the specific compound, and similar factors well known in the art of medicine. For example, it is a common method in the art to increase gradually the dose of compound from a level lower than that for achieving desired therapeutic effects to a level enough to achieve the desired therapeutic effects. In general, the dose of a compound of formula I for a mammal especially a human being can be 0.001-1000 mg/kg body weight per day, such as 0.01-100 mg/kg body weight per day, 0.01-10 mg/kg body weight per day.

A pharmaceutical composition comprising an effective amount of the compound of the present invention can be prepared by using a pharmaceutically acceptable carrier well-known by those skilled in the art. Hence, the present invention further provides a pharmaceutical composition comprising the compound of the present invention formulated with one or more non-toxic pharmaceutically acceptable carrier. The pharmaceutical composition can be specifically formulated in solid or liquid form for oral administration, parenteral injection or rectal administration.

The pharmaceutical composition can be formulated in many dosage forms for facilitating administration, for example, oral preparations (such as tablets, capsules, solutions or suspensions); injectable preparations (such as injectable solutions or suspensions, or injectable dry powders that can be immediately used by adding water before injection). The carrier in the pharmaceutical composition comprises for oral preparations: binders (such as starch, typically being starches of corn, wheat or rice, gelatin, methylcellulose, sodium carboxymethylcellulose and/or polyvinylpyrrolidone), diluents (such as lactose, dextrose, sucrose, mannitol, sorbitol, cellulose, and/or glycerol), lubricants (such as silicon dioxide, talc, stearic acid or salts thereof, typically being magnesium stearate or calcium stearate, and/or polyethylene glycol), if desired, further comprises disintegrating agents such as starch, agar, alginic acid or salts thereof, typically sodium alginate, and/or effervescence mixtures, co-solvents, stabilizing agents, suspending agents, coloring agent, flavoring agent, etc.; for injectable preparations: preservatives, solubilizing agents, stabilizing agents etc.; for topical preparations: substrates, diluents, lubricants, preservatives, etc. The pharmaceutical preparations can be adminstered orally or parenterally (such as intravenously, subcutaneously or topically), and if some drugs are not stable in gastral conditions, they can be formulated enteric coated tablets.

More specifically, the pharmaceutical composition of the present invention can be administrated orally, rectally, parenterally, endoluminally, endovaginally, intraperitoneally, topically (such as via powder, ointment or drops), buccally to a human or other mammal, or administrated as oral spray or nasal spray. The term "parenteral" in the context refers to administration manners including intravenous, intramuscular, intraperitoneal, intrathoracic, subcutaneous and intraarticular injection or transfusion.

The composition suitable for parenteral injection can comprise physiologically acceptable sterile aqueous or nonaqueous solvent, dispersant, suspending agent, or emulsifying agent, as well as sterile dispersant for reforming a sterile injectable solution or dispersion. The examples of suitable aqueous or nonaqueous carriers, diluents, solvents or media include water, ethanol, polyols (propylene glycol, polyethylene glycol, glycerol, etc.), vegetable oil (such as olive oil), injectable organic esters such as ethyl oleate and suitable mixtures thereof.

These compositions can further comprise excipients, such as preservative, wetting agent, emulsifying agent and dispersant. The use of various antibacterial agents and antifungal agents, such as nipagins, nautisan, phenol, sorbic acid, etc. can ensure effects of combating microorganisms. It is also desired to comprise isotonizing agents such as sugars, sodium chloride, etc. The use of substances for absorption delay, such as aluminium monostearate and gelatin, can achieve the prolonged absorption of injectable dosage form.

Besides the active compound, the suspension can further comprise a suspending agent, such as ethoxylated isooctadecanol, polyoxyethylene sorbitol and polyoxyethylene sorbitan, microcrystalline cellulose, meta-aluminum hydroxide, bentonite, agar and tragacanth gum, or mixtures of these substances.

In some cases, it is desired to reduce the absorption rate of subcutaneously or intramuscularly administered drug for prolonging the effect of drug. This can be reached by using a liquid suspension of crystal or amorphous form with poor water solubility. Thus, the absorption rate of drug depends on its dissolution rate, while the dissolution rate depends on the size and form of crystal. Or, the delayed absorption of drug in parenteral administration can be reached by dissolving or dispersing the drug in an oil medium.

An injectable depot dosage form can be prepared by forming microcapsule substrate of drug in a biodegradable polymer such as polylactide-polyglycolide. The release rate of drug can be controlled according to the ratio of drug to polymer and the properties of the specifically used polymer. Other examples of biodegradable polymer comprise poly(orthoesters) and poly(anhydrides). The injectable depot dosage form can also be prepared by embedding drug in a liposome or microemulsion compatible to body tissues.

The injectable preparation can be sterilized by filtration using a bacterial-removing filter or by incorporating a sterilizing agent in form of sterile solid composition, and the solid composition can be dissolved or dispersed in sterile water or other sterile injectable media before clinical application.

The compound of the present invention or composition thereof can be administrated orally or parenterally. Those for oral administration can be tablets, capsules, coated dosage form, and pharmaceutical preparations for parenteral administration can be injections and suppository. These preparations are prepared according to methods well-known by those skilled in the art. In order to manufacture tablets, capsules and coated dosage forms, the used excipients are commonly used excipients, such as starch, gelatin, arabic gum, silica, polyethylene glycol, the solvents used for liquid dosage forms are water, ethanol, propylene glycol, vegetable oils (such as corn oil, peanut oil, oliver oil, etc.). The preparations comprising the compound of the present invention can further comprise other excipients, such as surfactants, lubricants, disintegrants, preservatives, flavoring agent and coloring agent, etc. In tablets, capsules, coated dosage forms, injections and suppositories, the dose of the compound of formula I of the present invention is expressed in an amount of the compound existed in unit dosage form. In unit dosage form, the amount of the compound of formula I of the present invention usually is 1-5000 mg, a preferable unit dosage form contains 10-500 mg, a more preferable unit dosage form contains 20-300 mg. Specifically, the solid dosage form for oral administration as provided in the present invention comprise capsules, tablets, pills, powders and granules. In such solid dosage forms, the active compound can be mixed with at least one inert pharmaceutically acceptable excipient or carrier such as sodium citrate or dicalcium phosphate and/or the following substances: a) filler or bulking agent, such as starch, lactose, sucrose, glucose, mannitol and silicic acid; b) binding agent, such as carboxymethyl cellulose, alginate, gelatin, polyvinyl pyrrolidone, sucrose, and arabic gum; c) humectant, such as glycerol; d) disintegrating agent, such as agar, calcium carbonate, potato or cassaya starch, alginic acid, some silicates and sodium carbonate; e) solution blocking agent, such as paraffin wax; f) absorption accelerator, such as quaternary ammonium compounds; g) wetting agent, such as cetanol and glycerol monostearate; h) adsorbent, such as kaolin and bentonite; and i) lubricant, such as talc, calcium stearate, magnesium stearate, solid polyethylene glycol, sodium dodecylsulfate and their mixtures. In the cases of capsules, tablets and pills, these dosage forms may also comprise a buffering agent.

A solid composition of similar type uses excipients such as lactose and high molecular weight polyethylene glycol which can also be used as fillers of soft capsules and hard capsules.

The solid dosage forms of tablets, dragees, capsules, pills and granules can be prepared with coating agents and shell materials such as enteric coating materials and other coating materials well-known in the field of medical preparations. These solid dosage forms can optionally comprise sunscreening agent, and their composition can allow they merely or preferentially release active ingredient at some sites of intestinal tract optionally in a delayed manner. Examples of embedding composition comprise high molecular materials and waxes. If appropriate, the active compound can be formulated in form of microcapsules with one or more aforementioned excipients.

The liquid dosage form for oral administration comprises pharmaceutically acceptable emulsifying agent, solvent, suspending agent, syrup and elixir. Besides the active compound, the liquid dosage form may further comprise an inert diluent commonly used in the art, such as water or other solvent, solubilizer and emulsifying agent, such as ethanol, isopropanol, ethyl carbonate, ethyl acetate, benzyl alcohol, benzyl benzoate, propylene glycol, butane-1,3-diol, dimethyl formamide, oils (such as cottonseed oil, peanut oil, corn oil, embryo oil, olive oil, castor oil, and sesame oil), glycerol, tetrahydrofurfuryl alcohol, fatty acid esters of polyethylene glycol and sorbitan, and their mixtures. Besides inert diluents, the compositions for oral administration can further comprise excipients, such as wetting agents, emulsifying agents and suspending agents, sweeting agents, flavoring agent and flavors.

The composition for rectal or vaginal administration is preferably a suppository. The suppository can be prepared by mixing the compound of the present invention with a suitable non-irritative excipient or carrier, such as cocoa butter, polyethylene glycol or suppository wax, they can be solid at room temperature, but liquid at body temperature, and can release an active compound in rectal lumen or vaginal canal.

It is also desired to use the compound of the present invention for topical administration. The dosage form of the compound of the present invention for topical administration comprises powder, spray, ointment and inhalation. The active compound and a pharmaceutically acceptable carrier can be mixed under sterile conditions with any desired preservative, buffering agent or propellant. Ophthalmic preparation, eye salve, powder and solution are all in the scope of the present invention.

The compound of the present invention can be adminstered in a form of liposome. It is well known in the art, liposome usually is prepared by using phospholipid or other lipides. Liposome is formed with monolayer or multilayer hydrated liquid crystal which is dispersed in an aqueous medium. Any non-toxic, physiologically acceptable and metabolizable lipides capable of forming liposome can be usable. The composition of the present invention in liposome form can comprise stabilizing agent, preservative, excipient, besides the compound of the present invention. Preferable lipides are natural and synthetic phospholipids and phosphatidylcholines (lecithin), they can be used solely or together. The methods for forming liposome are well-known in the art. References can be seen, for example, Prescott, Ed., Methods in Cell Biology, Volume XIV, Academic Press, New York, N.Y. (1976), p. 33.

The inventors of the present application has surprisedly found that the quinazoline derivatives of formula I exhibit an inhibitory activity on both EGFR and Her2 tyrosine kinases, and in the meantime, inhibit cell strains in which EGFR and Her2 tyrosine kinases are highly expressed. Hence, the compound of the present invention can be used for treatment of diseases mediated solely or partially by EGFR and Her2 receptor tyrosine kinase, mainly by inhibiting one or more tyrosine kinases of EGFR family, and generating anti-proliferation, anti-migration and apoptosis-promoting effects by inhibiting the kinase activity. Specifically, by an inhibitory effect on EGFR and Her2 tyrosine kinases, the compound of the present invention can be used for the prophylaxis and treatment of one or more tumors sensitive to erbB receptor tyrosine kinase, especially EGF driven tumors and tumors in which EGFR or Her2 are highly expressed, including solid tumors such as cancers of bile duct, bone, bladder, brain/central nervous system, breast, colorectum, endometrium, stomach, head and neck, liver, lung (especially nonsmall-cell lung cancer), neuron, gullet, ovary, pancreatic gland, kidney, skin, testis, thyroid gland, uterus and vulva, and non-solid tumors such as leukemia, multiple myeloma, or lymphoma.

EXAMPLES

The present invention is further illustrated with specific preparation examples and biological test examples, and it should be understood that these examples and test examples are merely used for demonstration in details but not for limiting the present invention in any way.

The materials and methods used in examples are generally and/or specifically described in the present invention. Although many materials and operation methods used for fulfilling the purpose of the present invention are known in the art, they are still described detailed as possible. Those skilled in the art clearly know that if not described particularly, the materials and methods used in the present invention are well known in the art.

In the present invention, unless described otherwise, (i) temperature is expressed in centigrade (° C.), operations are performed at room temperature or environmental temperature; (ii) organic solvent is dried with anhydrous sodium sulfate, the evaporization of solvent is performed by using a rotary evaporator under reduced vacuum and a bath temperature of not higher than 60° C.; (iii) reaction procedure is monitored by using thin-layer chromatography (TLC); (iv) a final product has satisfactory proton nuclear magnetic resonance spectrum ($^1$H-NMR) and mass spectrum (MS) data.

Example 1

Synthesis of N-(4-(3-fluorobenzyloxy)-3-chlorophenyl)-6-(5-((2-(sulfamoyl)ethylamino)methyl)-2-furyl)-quinazolin-4-amine (Compound 1)

a. Synthesis of Amino-Cbz Protected Sodium Taurate

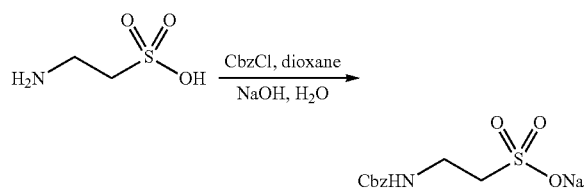

25.0 g of taurine was dissolved in 200 ml of 1M NaOH solution, and a solution of carbobenzoxy chloride (CbzCl, 51 g) in dioxane and 300 ml of 1M sodium hydroxide solution were added dropwise simultaneously under vigorous agitation. Upon the end of the dropping, the mixture was stirred for 1 hour at room temperature, the water phase was extracted with ethyl acetate, and concentrated the reaction under a reduced pressure to obtain 46.1 g of white solid, yield 82%.

b. Synthesis of 2-benzyloxyformamidoethylsulfonyl chloride

In a reaction flask, 20.0 g of amino-Cbz protected sodium taurate, SOCl$_2$ (30 ml) and DMF 1 ml were added. The mixture was reacted under refluxing for 3 h, cooled to room temperature, filtrated, and distilled under a reduced pressure to remove the solvent to obtain 17.9 g of oily product, yield 91%.

c. Synthesis of 2-benzyloxyformamidoethylsulfonamide

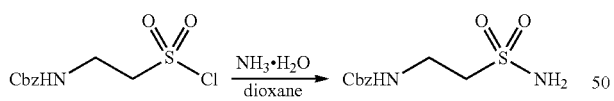

In a reaction flask, 100 ml of aqueous ammonia and 100 ml of dioxane were added, and a solution of 17.9 g 2-benzyloxyformamidoethylsulfonyl chloride in acetonitrile (30 ml) was added dropwise under ice-bath condition. The mixture was stirred for 2 h at room temperature. Upon the end of the dropping, the mixture was concentrated under a reduced pressure, and was then filtered, the filter cake was washed with water, and dried to obtain 12.3 g of white solid, yield 74%.

d. Synthesis of 2-formamidoethylsulfonamide

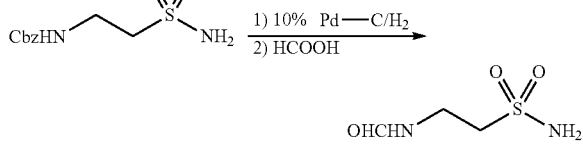

In a reaction flask, 10.3 g of 2-benzyloxyformamidoethylsulfonamide, 10% Pd/C (3.0 g) and 600 ml of methanol were added. The mixture was stirred at room temperature overnight under hydrogen atmosphere, added with 35 ml of formic acid, stirred for 30 min, filtered, and concentrated under a reduced pressure to obtain 5.6 g of oily product, yield 93%.

e. Synthesis of 2-sulfonamidoethylamine hydrochloride

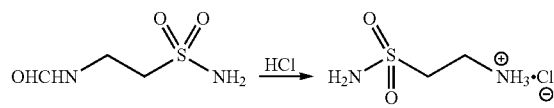

2-formamidoethylsulfonamide was added to anhydrous diethyl ether. The mixture was stirred for 3 h under hydrogen chloride gas, filtrated, the filter cake was washed with anhydrous diethyl ether, and dried to obtain 4.6 g of white solid, yield 87%.

f. Synthesis of N-(4-(3-fluorobenzyloxy)-3-chlorophenyl)-6-(5-((2-(sulfamoyl)ethylamino)methyl)-2-furyl)-quinazolin-4-amine

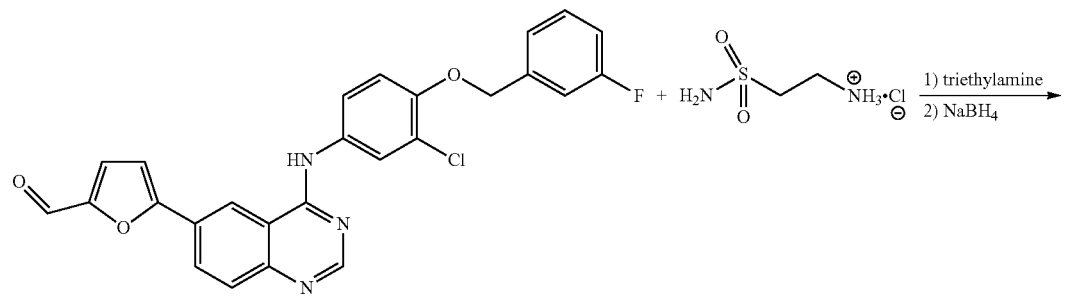

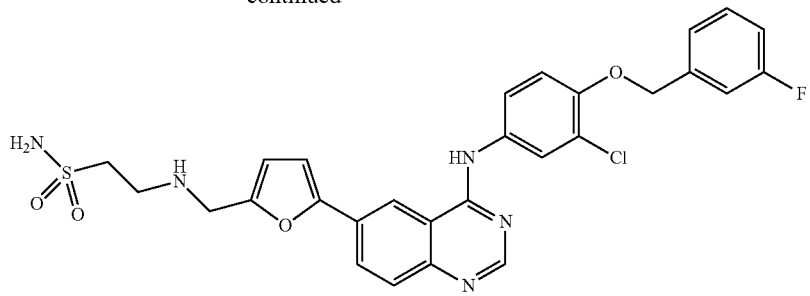

2.4 g of compound 5-(4-(4-(3-fluorobenzyloxy)-3-chloroanilino)-6-quinazolinyl)furan-2-formaldehyde was dissolved in the mixture of dichloromethane/methanol (3:1). The mixture was added with 1.0 g of triethylamine, stirred for 10 min, added with 1.6 g of 2-aminoethylsulfonamide hydrochloride, and stirred at room temperature. Upon consumption of the starting materials detected by TLC, 0.57 g of sodium borohydride was added in batches under ice-bath. Upon the end of reaction detected by TLC, dichloromethane (q.s.) was added. The mixture was washed with saturated ammonium chloride solution and then with saturated sodium chloride solution, dried over anhydrous sodium sulfate, and subjected to a column chromatography to obtain 2.2 g of yellow solid, yield 74%.

$^1$H NM (600 MHz, DMSO-$d_6$, δppm): 10.06 (s, 1H), 9.1 (s, 1H), 8.58 (s, 1H), 8.20 (dd, 1H, J=1.8 Hz, J=9 Hz), 8.15 (s, 1H), 7.87 (d, 1H, J=7.8 Hz), 7.82 (d, 1H, J=8.4 Hz), 7.48 (d, 1H, J=7.8 Hz), 7.34 (d, 1H, J=7.8 Hz), 7.32 (s, 1H), 7.29 (d, 1H, J=9 Hz), 7.21 (d, 1H, J=2.4 Hz), 7.18 (d, 1H, J=1.8 Hz), 7.12 (s, 1H), 5.23 (s, 2H), 3.42 (m, 2H), 3.35 (s, 2H), 4.23 (s, 2H), 3.13 (m, 2H).

MS (m/z): [M+H]$^+$ 582.1.

Compound 1 was dissolved in tetrahydrofuran, and the solution was slowly added dropwise to a solution of p-toluenesulfonic acid in ethanol. The mixture was heated under reflux for 2 h, precipitated to give a flavo-green deposite, filtrated and dried to obtain a p-tosylate of compound 1.

Example 2

Synthesis of N-(4-(3-fluorobenzyloxy)-3-chlorophenyl)-6-(5-((2-(methylsulfinyl)ethylamino)methyl)-2-furyl)-quinazolin-4-amine (Compound 2)

a. Synthesis of Boc Protected 2-mercaptoethylamine

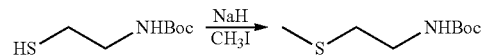

In a reaction flask, 35.3 g of ditertbutyl dicarbonate, 20.4 g of 2-mercaptoethylamine hydrochloride and 200 ml of dichloromethane were added. The mixture was added in batches with 25 ml of triethylamine under ice-bath condition, and was then stirred at room temperature overnight, added with an excessive amount of 0.5M hydrochloric acid solution for washing. The organic layer was washed with saturated sodium chloride solution, dried over anhydrous sodium sulfate, and distilled of the solvents to obtain 8 g of oily liquid, yield 87%.

b. Synthesis of Boc Protected 2-methylthioethylamine

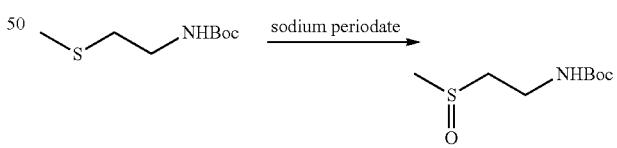

4.8 g of NaH was added in batches to the solution of 28 g Boc protected 2-mercaptoethylamine in anhydrous tetrahydrofuran (250 ml) under ice-bath and nitrogen-protection. The temperature was increased to room temperature, and the mixture was reacted for 1 h, added dropwise with 12 ml of iodomethane in tetrahydrofuran under ice-bath condition. Upon the end of the dropping, the reaction was performed at room temperature for about 1 h, and saturated sodium carbonate solution was added to quench the reaction. The reaction liquid was poured into water, and the mixture was extracted with ethyl acetate. The organic phase was washed with saturated sodium chloride solution, dried over anhydrous sodium sulfate, and distillated off the solvent to obtain oily liquid which was subjected to a column chromatography to obtain 14.2 g of the desired product, yield 47%.

c. Synthesis of Boc Protected 2-methylsulfinylethylamine

Under ice-bath condition, 14.0 g of Boc protected 2-methylthioethylamine was dissolved in methanol, and sodium periodate aqueous solution was added dropwise. Upon the end of the addition, the mixture was reacted under stirring at room temperature overnight, filtrated, and filter cake was washed with dichloromethane. The filtrate was distillated under a reduced pressure to remove the organic reagents, added with saturated sodium chloride solution, extracted with ethyl acetate, dried over anhydrous magnesium sulfate, filtrated, and distilled under a reduced pressure to remove the solvent to obtain 13.2 g of oily product, yield 87%.

d. Synthesis of Boc Protected 2-methylsulfinylethylamine hydrochloride

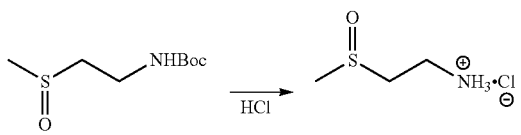

12 g of Boc protected 2-methylsulfinylethylamine was dissolved in anhydrous diethyl ether, and fed with hydrogen chloride gas. Upon consumption of the starting materials detected by TLC, the mixture was distilled under a reduced pressure to remove the solvent to obtain 6.8 g of oily product, yield 82%.

e. Synthesis of N-(4-(3-fluorobenzyloxy)-3-chlorophenyl)-6-(5-((2-(methylsulfinyl)ethylamino)methyl)-2-furyl)-quinazolin-4-amine

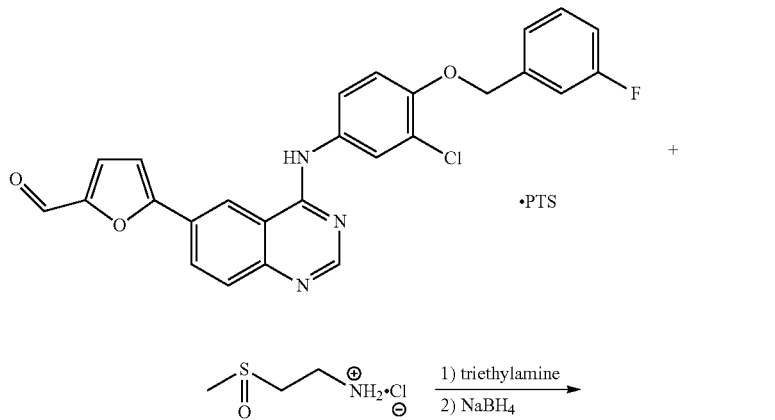

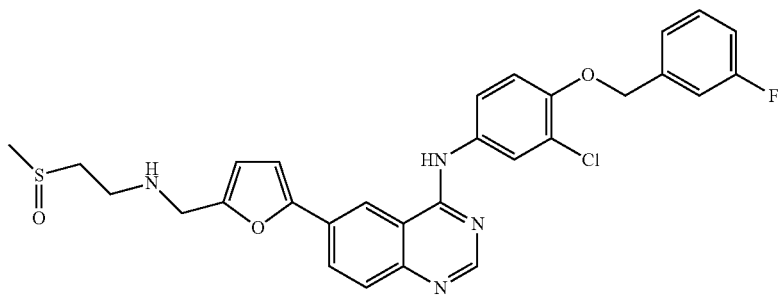

12 g of compound 5-(4-(4-(3-fluorobenzyloxy)-3-chloroanilino)-6-quinazolinyl)furan-2-formaldehyde p-tosylate was dissolved in the mixture of dichloromethane/methanol (3:1). The mixture was added with 12 ml of triethylamine, stirred for 10 min, added with 6.0 g of 2-methylsulfinylethylamine hydrochloride, and stirred at room temperature. Upon consumption of the starting materials detected by TLC, 2.0 g of sodium borohydride was added in batches under ice-bath. Upon the end of reaction detected by TLC, dichloromethane (q.s.) was added. The mixture was washed with saturated ammonium chloride and then with saturated ammonium chloride, dried over anhydrous sodium sulfate, and subjected to a column chromatography to obtain 7.3 g of yellow solid, yield 69%.

$^1$H-NM (600 MHz, DMSO-$d_6$, δppm): 9.92 (s, 1H), 9.044 (s, 1H), 8.92 (s, 1H), 8.41 (t, 1H, J=6.6 Hz), 7.93 (d, 1H, J=7.8 Hz), 7.64 (dd, 1H, J=2.4 Hz, J=9 Hz), 7.50 (d, 1H, J=7.8 Hz), 7.48 (d, 1H, J=9.6 Hz), 7.36 (d, 1H, J=9 Hz), 7.25 (d, 1H, J=3.0 Hz), 7.22 (dd, 1H, J=2.4 Hz, J=9 Hz), 7.11 (d, 1H, J=7.2 Hz), 7.25 (d, 1H, J=3.0 Hz), 5.32 (s, 2H), 4.47 (s, 2H), 3.51 (t, 2H, J=7.2 Hz), 2.67 (t, 2H, J=7.2 Hz), 2.29 (s, 3H).

MS (m/z): [M+H]$^+$ 565.5.

Example 3

Synthesis of N-(4-(3-fluorobenzyloxy)-3-chlorophenyl)-6-(5-((2-(methylthio)ethylamino)methyl)-2-furyl)-quinazolin-4-amine (Compound 3)

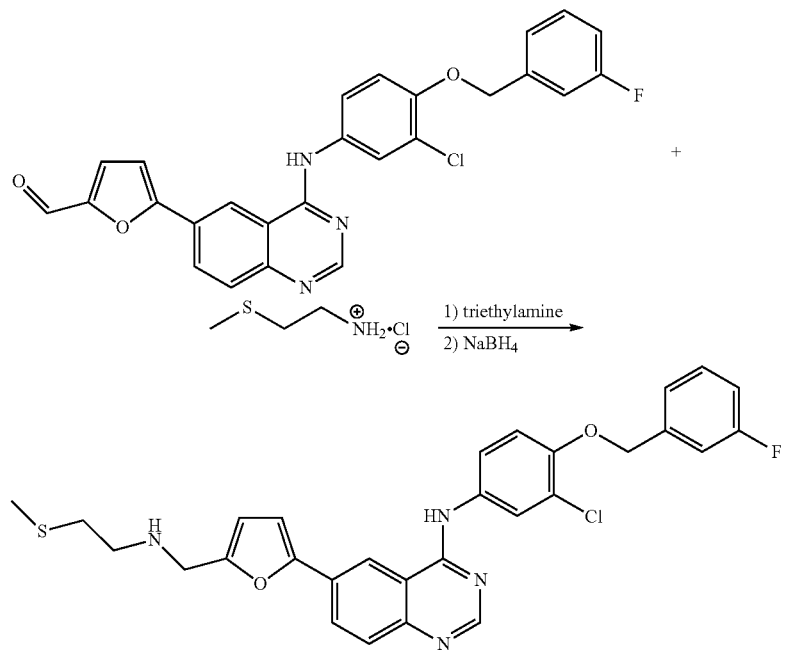

10.0 g of compound 5-(4-(4-(3-fluorobenzyloxy)-3-chloroanilino)-6-quinazolinyl)furan-2-formaldehyde was dissolved in the mixture of dichloromethane/methanol (3:1). The mixture was added with 4.3 g of triethylamine, stirred for 10 min, added with 6.9 g of 2-methylthioethylamine hydrochloride, and stirred at room temperature. Upon consumption of the starting materials detected by TLC, 2.4 g of sodium borohydride was added in batches under ice-bath. Upon the end of reaction detected by TLC, dichloromethane (q.s.) was added. The mixture was washed with saturated ammonium chloride and then with saturated sodium chloride, dried over anhydrous sodium sulfate, and subjected to a column chromatography to obtain 6.5 g of yellow solid, yield 56%.

$^1$H-NM (600 MHz, DMSO-$d_6$, δppm): 9.93 (s, 1H), 8.73 (s, 1H), 8.55 (s, 1H), 8.16 (d, 1H, J=2.4 Hz), 8.01 (d, 1H, J=2.4 Hz), 7.80 (d, 1H, J=7.4 Hz), 7.74 (dd, 1H, J=2.4 Hz, J=9 Hz), 7.45 (m, 1H), 7.34 (d, 1H, J=7.8 Hz), 7.32 (s, 1H), 7.29 (d, 1H, J=8.4 Hz), 7.19 (t, 1H, J=8.4 Hz), 7.05 (d, 1H, J=3.0 Hz), 6.48 (d, 1H, J=3.0 Hz), 5.25 (s, 2H), 3.83 (s, 2H), 2.77 (t, 2H, J=7.2 Hz), 2.59 (t, 2H, J=7.2 Hz), 2.04 (s, 3H).

MS (m/z): [M+H]$^+$ 549.5.

Example 4

Synthesis of N-(4-(3-fluorobenzyloxy)-3-chlorophenyl)-6-(5-((2-(methylsulfonamido)ethylamino)methyl)-2-furyl)-quinazolin-4-amine (Compound 4)

a. Synthesis of tert-butyl 2-aminoethylaminoformate

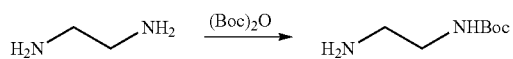

In a 500 ml reaction flask, 30 ml of ethylenediamine was added, and 18.0 g of ditertbutyl dicarbonate in dichloromethane (200 ml) was added dropwise under ice-bath condition, the temperature was naturally warmed to room temperature and the reaction was conducted overnight. The mixture was added with 100 ml of dichloromethane, washed with saturated sodium carbonate solution and then with saturated sodium chloride solution, dried over anhydrous sodium sulfate, filtrated, and distilled under a reduced pressure to remove the solvent to obtain 10.9 g of light yellow oily liquid, yield 82.6%.

b. Synthesis of tert-butyl 2-methylsulfonamidoethylaminoformate

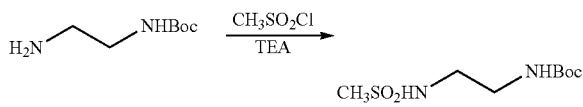

In a 1000 ml reaction flask, 36.9 g of tert-butyl 2-aminoethylaminoformate and 200 ml of dichloromethane were added. The mixture was stirred by an electromagnetic stirrer, cooled with ice-bath, added with 96 ml of triethylamine, slowly added dropwise with 35.9 g of methylsulfonyl chloride in 200 ml of dichloromethane. The temperature of the mixture was naturally warmed to room temperature and the mixture was conducted overnight. The mixture was added dropwise with ice-water to quench reaction, the organic layer was separated, and the water layer was extracted with dichloromethane. The organic layers were combined, washed sequentially with 5 mol/L dilute hydrochloric acid, saturated sodium bicarbonate solution and saturated sodium chloride solution, dried over anhydrous sodium sulfate, filtrated, and distilled under a reduced pressure to remove the solvent to obtain 28.6 g of brown yellow solid, yield 52.1%.

c. Synthesis of N-(2-aminoethyl)methylsulfonamide hydrochloride

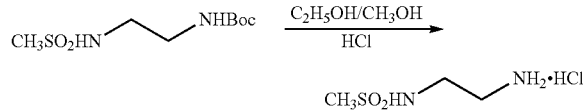

In a 500 ml reaction flask, tert-butyl 2-methylsulfonamidoethylaminoformate (25 g) and 350 ml of a mixture of ethanol and methanol were added. The mixture was stirred by an electromagnetic stirrer, fed with dry hydrogen chloride gas for 3 h, stirred at room temperature overnight, concentrated under a reduced pressure to a small volume, subjected to suction filtration to obtain 14.6 g of brown-gray powdery solid, yield 79.3%.

d. Synthesis of N-(4-(3-fluorobenzyloxy)-3-chlorophenyl)-6-(5-((2-(methylsulfonamido)ethylamino)methyl)-2-furyl)-quinazolin-4-amine

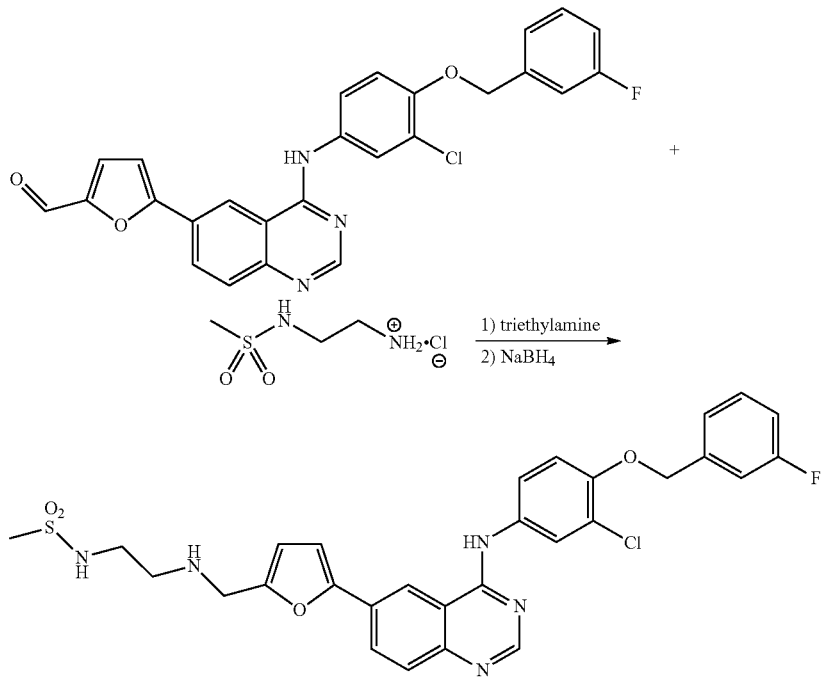

At room temperature, 10.0 g of compound 5-(4-(4-(3-fluorobenzyloxy)-3-chloroanilino)-6-quinazolinyl)furan-2-formaldehyde, 6.5 g of compound N-(2-aminoethyl)methanesulfonamide hydrochloride, and 14.6 g of triethylamine in the mixture of dichloromethane/methanol (3:1) were stirred overnight, then cooled with ice-bath to 0° C., and 1.4 g of sodium borohydride was added at that temperature. The mixture was warmed to room temperature, stirred overnight, saturated sodium bicarbonate was added to quench the reaction, and extracted with ethyl acetate. The organic phase was washed with saturated sodium chloride solution, dried over anhydrous sodium sulfate, and subjected to a column chromatography to obtain 5.7 g of the desired product, yield 45.0%.

$^1$H-NMR (300 MHz, CDCl$_3$, δppm): 8.65 (s, 1H), 8.62 (s, 1H), 8.28 (s, 1H), 7.84~7.73 (m, 3H), 7.53 (d, 1H, J=8.7 Hz), 7.33-7.28 (m, 1H), 7.19~7.15 (m, 2H), 6.98 (t, 1H, J=8.4 Hz), 6.86 (d, 1H J=4.5 Hz), 6.57 (d, 1H, J=1.8 Hz), 6.20 (d, 1H, J=1.8 Hz), 5.04 (s, 2H), 3.73 (s, 2H), 3.18 (t, 2H, J=8.4 Hz), 2.87 (s, 3H), 2.78 (t, 2H, J=8.4);

$^{13}$C-NMR (75 MHz, CDCl$_3$, δppm): 164.4, 161.2, 157.8, 154.4, 153.7, 152.2, 150.7, 148.9, 139.0, 138.9, 132.4, 130.1, 130.0, 124.9, 128.6, 128.5, 124.9, 122.7, 122.4, 122.3, 115.3, 115.1, 114.8, 114.5, 113.9, 113.6, 109.7, 107.1, 70.1, 47.4, 45.2, 42.2, 40.0;

HR-MS (m/z): calculated: C$_{29}$H$_{27}$ClFN$_5$O$_4$S [M+H]$^+$ 596.1529, measured: 596.1533.

Example 5

Synthesis of N-(4-(3-fluorobenzyloxy)-3-chlorophenyl)-6-(5-((2-(2,2,2-trifluoroethylsulfonyl)ethylamino)methyl)-2-furyl)-quinazolin-4-amine (Compound 5)

a. Synthesis of 2,2,2-trifluoroethyl-(4-methylphenyl)sulfonate

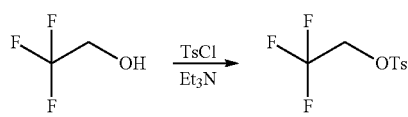 [SMILES: "Et3N" ; OCC(F)(F)F ; "TsCl" ; Cc1ccc(S(=O)(=O)OCC(F)(F)F)cc1]

2.1 ml of 2,2,2-trifluoroethanol and 4.4 ml of triethylamine were added to 100 ml of dichloromethane, and 5.0 g of p-toluenesulfonyl chloride in batches under ice-bath condition. Upon the end of the addition, the mixture was warmed to room temperature and stirred overnight. The mixture was washed with water and then with saturated sodium chloride solution, dried over anhydrous sodium sulfate, and distilled to remove the solvent to obtain 5.9 g of light yellow oily liquid, yield 98.7%.

b. Synthesis of tert-butyl 2-mercaptoethylaminoformate

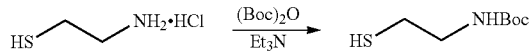

3.5 g of ditertbutyl dicarbonate and 2.0 g of 2-mercaptoethylamine hydrochloride were added to 200 ml of dichloromethane, and 1 of triethylamine was added dropwise under ice-bath condition. The mixture was warmed to room temperature and stirred overnight. The mixture was washed with 0.5M hydrochloric acid aqueous solution and then with saturated sodium chloride solution, dried over anhydrous sodium sulfate, and distilled to remove the solvent to obtain 2.7 g of oily liquid, yield 87.1%.

c. Synthesis of tert-butyl 2-(2,2,2-trifluoroethylthio)ethylaminoformate

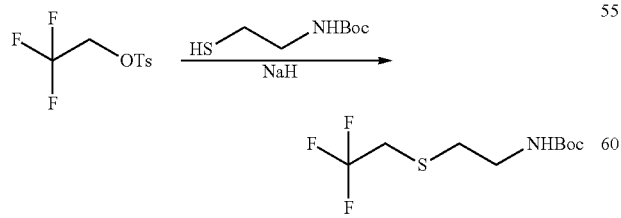

1.7 g of sodium hydride was added to 30 ml of dry dimethylformamide, and then 7.5 g of tert-butyl 2-mercaptoethylaminoformate. Upon the end of the addition, the mixture was stirred for 1 h, and then slowly added with 2,2,2-trifluoroethyl (4-methylphenyl)sulfonate. Upon the end of the addition, the mixture was warmed to room temperature, and stirred overnight. The mixture was poured to water, extracted with diethyl ether, washed with 0.5M sodium hydroxide aqueous solution and then with saturated sodium chloride solution, dried over anhydrous sodium sulfate, distilled to remove the solvent, and subjected to a column chromatography to obtain 5.4 g of light yellow oily liquid, yield 53.8%.

d. Synthesis of tert-butyl 2-(2,2,2-trifluoroethylsulfonyl)ethylaminoformate

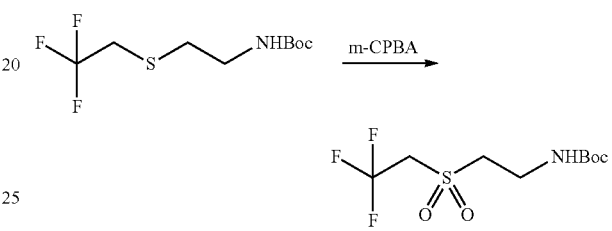

3.9 g of tert-butyl 2-(2,2,2-trifluoroethylthio)ethylaminoformate was dissolved in 50 ml of dichloromethane, and 12.2 g of m-chloroperoxybenzoic acid was added in batches under ice-bath condition. The reaction was warmed to room temperature, and stirred for 5 h. The reaction was added with saturated sodium bisulfite aqueous solution to quench the reaction, and extracted with dichloromethane. The organic layers were combined, washed with saturated sodium carbonate aqueous solution and then with saturated sodium chloride aqueous solution, dried over anhydrous sodium sulfate, and distilled to remove the solvent to obtain 3.9 g of white solid, yield 89.4%.

e. Synthesis of 2-(2,2,2-trifluoroethylsulfonyl)ethylammonium chloride

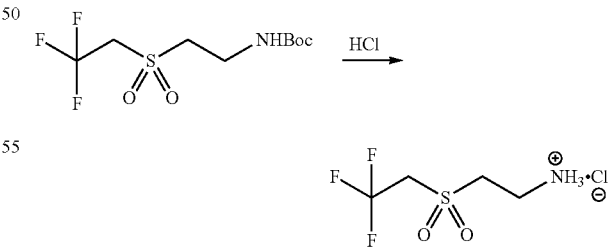

3.9 g of tert-butyl 2-(2,2,2-trifluoroethylsulfonyl)ethylaminoformate was added to 60 ml of anhydrous diethyl ether. The mixture was stirred at room temperature overnight under hydrogen chloride gas, subjected to suction filtration, and washed with diethyl ether to obtain 2.7 g of white solid, yield 87.7%.

f. Synthesis of N-(4-(3-fluorobenzyloxy)-3-chlorophenyl)-6-(5-((2-(2,2,2-trifluoroethylsulfonyl)ethylamino)methyl)-2-furyl)-quinazolin-4-amine

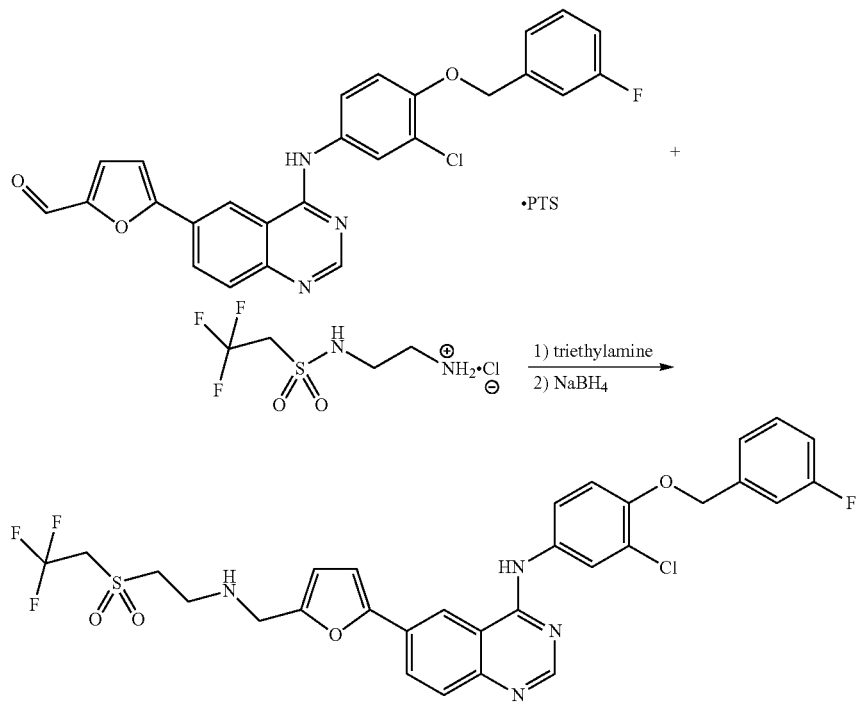

At room temperature, 10.0 g of compound 5-(4-(4-(3-fluorobenzyloxy)-3-chloroanilino)-6-quinazolinyl)furan-2-formaldehyde p-tosylate, 7.1 g of compound 2-(2,2,2-trifluoroethylsulfonyl)ethylamine hydrochloride, 11 ml of triethylamine and 20 g of anhydrous sodium sulfate in the mixture of dichloromethane/methanol (3:1) were stirred overnight, and then cooled to 0° C. with ice bath. The mixture was added with 1.8 g of sodium borohydride at that temperature, naturally warmed to room temperature, and stirred overnight. The mixture was added with saturated sodium bicarbonate to quench the reaction, and extracted with ethyl acetate. The organic phase was washed with saturated sodium chloride solution, dried over anhydrous sodium sulfate, and subjected to a column chromatography to obtain 5.4 g of the desired product, yield 53.5%.

$^1$H-NMR (400 MHz, acetone-$d_6$, δppm): 9.33 (s, 1H), 8.77-8.75 (m, 2H), 8.30-8.28 (m, 1H), 8.24 (s, 1H), 7.97 (d, J=4.4 Hz, 1H), 7.90 (d, J=4.4 Hz, 1H), 7.61 (q, J=7.6 Hz, 1H), 7.53-7.35 (m, 3H), 7.24 (d, J=0.8 Hz, 1H), 7.28-7.24 (m, 1H), 7.08 (s, 1H), 6.60 (s, 1H), 5.42 (s, 2H), 4.73 (q, J=10 Hz, 2H). 3.60 (t, J=6.0 Hz, 2H), 3.40 (t, J=6.0 Hz, 2H);

$^{13}$C-NMR (100 MHz, acetone-$d_6$, δppm): 171.0, 165.3, 162.9, 158.9, 155.9, 155.5, 153.4, 151.6, 150.7, 141.2, 141.2, 134.7, 131.6, 131.5, 130.1, 129.7, 126.4, 125.0, 124.9, 123.3, 122.2, 116.9, 115.8, 115.0, 110.7, 108.6, 71.0, 57.5, 57.2, 56.9, 56.6, 46.6, 43.5, 33.8;

HR-MS (m/z): calculated: $C_{30}H_{25}ClF_4N_4O_4S$ [M+H]$^+$ 649.1294, measured: 649.1288.

Example 6

Synthesis of N-(4-(3-fluorobenzyloxy)-3-chlorophenyl)-6-(5-((2-(trifluoromethylsulfonyl)ethylamino)methyl)-2-furyl)-quinazolin-4-amine (Compound 6)

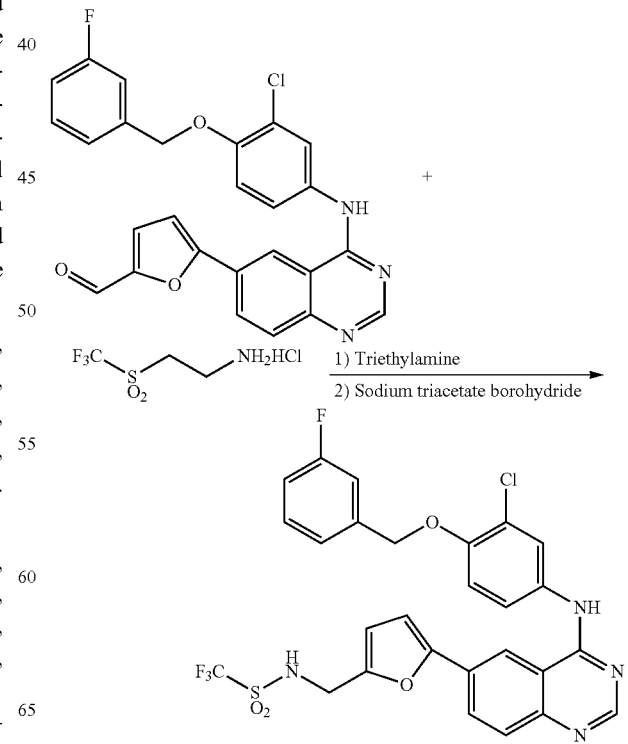

At room temperature, 240 mg of compound 5-(4-(4-(3-fluorobenzyloxy)-3-chloroanilino)-6-quinazolinyl)furan-2-formaldehyde, 120 mg of compound 2-trifluoromethylsulfonylethylamine hydrochloride, 0.2 ml of triethylamine were mixed in 10 ml of dichloromethane, and 0.2 ml glacial acetic acid was added. The mixture was stirred for 4 h, cooled to 0° C. with ice-bath at which temperature 500 mg of sodium triacetyloxyborohydride was added, then warmed to room temperature, further stirred for 12 h, added with saturated sodium bicarbonate to quench the reaction, and extracted with ethyl acetate. The organic phase was washed with saturated sodium chloride solution, dried over anhydrous sodium sulfate, and subjected to a column chromatography to obtain 35.7 mg of yellow solid, yield 11.1%.

$^1$H-NMR (400 MHz, CDCl$_3$, δppm): 8.70 (s, 1H), 8.27 (s, 1H), 7.98-7.96 (m, 1H), 7.90-7.88 (m, 2H0, 7.84 (d, J=1.2 Hz, 1H), 7.54 (dd, J=2.4 Hz, J=8.8 Hz, 1H), 7.39-7.34 (m, 1H), 7.24-7.22 (m, 1H), 7.04-6.97 (m, 2H), 6.76 (d, J=1.2 Hz, 1H), 6.45 (d, J=1.6 Hz, 1H), 5.17 (s, 2H), 3.92 (s, 2H), 3.55-3.49 (m, 2H), 3.37-3.34 (m, 2H);

$^{13}$C-NMR (100 MHz, CDCl$_3$, δppm): 164.20, 161.75, 157.80, 154.97, 153.55, 151.06, 149.77, 49.57, 139.14, 139.07, 132.14, 130.17, 130.09, 129.25, 128.80, 128.18, 125.18, 124.06, 23.40, 123.34, 122.45, 122.43, 122.29, 120.81, 117.56, 115.34, 115.01, 114.95, 114.74, 114.18, 114.08, 113.86, 112.46, 07.11, 70.37, 47.87, 46.12, 45.74;

HR-MS (m/z): calculated: C$_{29}$H$_{23}$ClF$_4$N$_4$O$_4$S [M+H]$^+$ 635.1137, measured: 635.1142.

N-(4-(3-fluorobenzyloxy)-3-chlorophenyl)-6-(5-((2-(methylsulfonyl)ethylamino)methyl)-2-furyl)-quinazolin-4-amine (Compound 61) can be readily obtained by using procedures similar to those of the process for preparing Compound 6, except that 2-trifluoromethylsulfonylethylamine hydrochloride was replaced with 2-methylsulfonyl-ethylamine hydrochloride.

Example 7

Preparation of the Other Compounds

The compounds of formula I as designated as Compounds 7 to 14 in the following table can be obtained by procedures similar to those of the corresponding examples as indicated above:

Biological Tests

The following tests can be used to determine the inhibitory activity of the compounds of the present invention on EGFR tyrosine kinase and the effects of the compounds of the present invention as NCI-N87 cell and BT474 cell inhibitors in vitro.

A) Determination of Phosphorylation of Protein Tyrosine Kinase

In vitro kinase analysis was performed by using HTScan EGF Receptor Kinase Assay Kit (#7909) and HTScan HER2/ErbB2 Kinase Assay Kit (#7058) from Cell Signaling Technology Company. Operation steps refer to the specification of the used kits, and the method was used to measure the inhibition effects of the compound to be tested on substrate peptide phosphorylation of EGFR or Her2 receptor tyrosine kinase. At room temperature, ATP and substrate peptide as well as the compound to be tested were incubated in kinase reaction buffer, after a period of incubation, a stop buffer was added to terminate the reaction and the sample was transferred to a streptavidin-coated 96-well plate, the plate was washed and the phosphorylation level of substrate peptide was detected by using HRP-marked antibody against substrate phosphorylation, colorated with TMB, terminated the reaction with 2M sulfuric acid. Absorption at 450 nm wavelength was detected, and IC$_{50}$ value (μM) was calculated. The results are given in Table 1.

B) Inhibition of Cell Proliferation

The test was performed by referring to the method as described by Rusnak et al., Cell Prolif, 2007, 40, 580-594. The test of cell proliferation inhibition used human breast cancer cells BT474 and human gastric cancer cell line NCI-N87, BT474 over-expressing Her2 receptor, N87 over-expressing EGFR and Her2 receptor.

In a Dulbecco Modified Eagle Medium (DMEM) comprising 10% fetal bovine serum, 2 mM glutamine and non-essential amino acids, cells were cultured at 37° C. in 5% CO$_2$ cell incubator, and trypsin/ethylenediamine tetraacetic acid (EDTA) were used to harvest cells in cell culture bottle. The cells were added to the 96-well cell culture plate, 4000/well (0.1 ml medium), adhering wall overnight, 0.1 ml of diluted

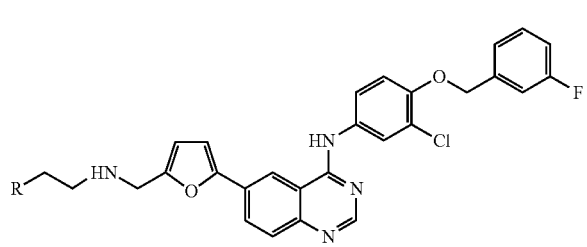

I

| Compound No. | R | Mass spectra (MS) |
|---|---|---|
| Compound 7 | CF$_3$S— | 603.3 [M + H]$^+$ |
| Compound 8 | CF$_3$S(O)— | 619.3 [M + H]$^+$ |
| Compound 9 | CF$_3$CH$_2$S— | 617.4 [M + H]$^+$ |
| Compound 10 | CF$_3$CH$_2$S(O)— | 633.4 [M + H]$^+$ |
| Compound 11 | CH$_3$CONH— | 560.1 [M + H]$^+$ |
| Compound 12 | CH$_3$NHS(O)$_2$— | 596.3 [M + H]$^+$ |
| Compound 13 | CH$_3$CH$_2$NHS(O)$_2$— | 610.3 [M + H]$^+$ |
| Compound 14 | CF$_3$CH$_2$S(O)$_2$NH— | 663.4 [M + H]$^+$ | solution of the compound to be tested was added, the final concentration of DMSO was 0.25%, the cell culture plate was incubated at 37° C. and 5% $CO_2$ condition for 72 h. The change of cell form was observed under microscope, then 50 μl 50% (mass/volume)trichloroacetic acid (TCA) was added to per well to fix cells. The final concentration of TCA was 10%, standing for 5 min and placing in 4° C. refrigerator for 1 h, the wells of the culture plate were washed with deionized water for 5 times to remove TCA, drained, dried in air until no wet trace was observed. 100 μl of 0.4% (mass/volume) SRB was added to each well, stood at room temperature for 10 min, the liquid in each well was discarded, then the wells were washed with 1% acetic acid for 5 times, dried in air, extracted with 150 μl of 10 mM Tris base (trihydroxymethylaminomethane, pH 10.5), the absorption at 540 nm wavelength was detected. The results of IC50 values (μM) are given in Table 1.

TABLE 1

Analysis of the inhibitory activity of the compound of the present invention on EGFR and Her2

| Tested substance | Analysis of in vitro kinase $IC_{50}$ (μM) | | Test of cell proliferation inhibition $IC_{50}$ (μM) | |
|---|---|---|---|---|
| | EGFR | Her2 | N87 | BT474 |
| Compound 1 | 0.00271 | 0.00155 | 0.00728 | 0.01330 |
| Compound 2 | 0.05267 | 0.02250 | 0.01266 | 0.01828 |
| Compound 3 | 0.05624 | 0.03455 | 0.02494 | 0.02337 |
| Compound 4 | 0.01554 | 0.00706 | 0.01783 | 0.01672 |
| Compound 5 | 0.01461 | 0.00808 | 0.03367 | 0.01885 |
| Compound 6 | 0.03240 | 0.02560 | 0.05455 | 0.04974 |

In the "test of cell proliferation inhibition" as one important test for evaluating biological activity of compound, it can be seen that the compound of the present invention has better biological activity.

In addition, in the same test, Compound 61 has biological activity results close to those of compound 6; Compounds 7 to 14 also have biological activity results close to compounds 2 or 3. The results show that the compounds of formula I of the present invention are inhibitors against effective tyrosine kinase.

C) Evaluation of In vivo Biological Activity

BALB/cA-nude mice, female, 4-6 weeks, body weight 22±2 g, were purchased from Shanghai SLAC Laboratory Animal Co. Ltd, raised in SPF grade environment.

1) Therapeutic Effect of the Present Compounds at a Single Dose on Human Gastric Cancer NCI-N87 Transplanted Tumor in Nude Mice:

In vitro cultured NCI-N87 cells were subcutaneously inoculated at right axillary fossa of nude mice, each was inoculated with about $5 \times 10^6$ cells, and passaged twice in vivo after tumor formation. Under sterile conditions, eugonic tumor tissues were cut into tumor pieces of about 1.5 $mm^3$, and inoculated at right axillary fossa of nude mice. Tumor diameters were measured by vernier caliper, the animals were randomly divided ($d_0$) after the tumors grew to 100-200 $mm^3$. Compounds 2, 3 and 5 and positive control (compound 61) in a dosage of 200 mg/kg were administered intragastrically, once per day, for consecutive 28 days, the control group was given equivalent amount of solvent. During administration period, the body weight of mice and the diameter of tumors were measured 3 times per week. The tumor volume and relative tumor volume were calculated according to the measured data, the formulation for calculating tumor volume (TV) is: $TV = \frac{1}{2} \times a \times b^2$, wherein a, b represent major diameter and minor diameter of tumor; the formulation for calculating relative tumor volume (RTV) is: $RTV = V_t/V_0$, wherein $V_0$ is the tumor volume measured when dividing groups for administration (i.e., $d_0$), $V_t$ is tumor volume measured each time. The evaluation index for antitumor activity is relative tumor growth rate T/C (%), the formulation for calculation thereof is: $T/C (\%) = (T_{RTV}/C_{RTV}) \times 100\%$, wherein $T_{RTV}$ is RTV of the therapeutic group, $C_{RTV}$ is RTV of the negative control. The formulation for calculating relative tumor inhibition rate is: $1 - T/C (\%)$. The relative tumor inhibition rate is ≥60%, statistical treatment shows P≤0.05, i.e., the drug is effective. The results of the test are shown in the following table:

TABLE 2

Experimental results of tumor inhibition of the present compounds at a single dose on human gastric cancer NCI-N87 transplanted tumor in nude mice

| Group | $d_0$ | | $d_{28}$ | | | | Rate of tumor inhibition $d_{21}$ (%) | P | Animal number in each group | |
|---|---|---|---|---|---|---|---|---|---|---|
| | $V_{ave}$ | SD | $V_{ave}$ | SD | RTV | SD | | | Total | Partial regression |
| Control | 152.72 | ±88.84 | 786.92 | ±752.93 | 4.838 | ±1.612 | 0 | — | 10 | 0 |
| Compound 2 | 165.77 | ±81.20 | 49.42 | ±61.40 | 0.251 | ±0.245 | 94.8 | 0.001 | 6 | 6 |
| Compound 3 | 164.69 | ±70.99 | 143.01 | ±150.40 | 0.743 | ±0.607 | 84.6 | 0.001 | 6 | 4 |
| Compound 5 | 169.55 | ±115.00 | 414.78 | ±270.89 | 2.574 | ±1.436 | 46.8 | 0.013 | 6 | 1 |
| Compound 61 | 160.30 | ±71.16 | 106.20 | ±180.54 | 0.495 | ±0.625 | 89.8 | 0.001 | 6 | 5 |

The results of in vivo activity screening test show that: as for human gastric cancer NCI-N87 nude mice-transplanted tumor model, the tumor inhibition rate of compound 2 (94.8%) is significantly higher than that of compound 61 (89.8%), the second is Compound 3, which has an activity (tumor inhibition rate: 84.6%) lower than that of compound 61. Six animals of the group for Compound 2 all showed tumor regression, five mice of the positive control group (Compound 61) showed tumor regression, and four animals of the group for Compound 3 showed tumor regression.

2) Therapeutic Effect of the Present Compounds at a Single Dosage on Human Ovarian Cancer SK-OV-3 Transplanted Tumor in Nude Mice:

Nude mice were subcutaneously inoculated with human ovarian cancer SK-OV-3 cells, after tumors grew to 60-150 $mm^3$, the animals were randomly divided into groups ($d_0$). The groups for Compounds 2, 3, 5 and positive control (Compound 61) were intragastrically administered with a dose of 200 mg/kg, once per day for consecutive 21 days, the control group was given an equivalent amount of solvent. During the administration period, the body weight of mice and the diameter of tumor were measured 3 times per week. The tumor volume, relative tumor inhibition rate and so on were calculated according to the aforementioned methods. The results of test are shown in Table 3:

The tumor inhibition test results of compound at different dosages on human ovarian cancer SK-OV-3 nude mice-transplanted tumor show that compound 2 and compound 3 both could inhibit the growth of human ovarian cancer SK-OV-3 nude mice-transplanted tumors in different extents, and the inhibition effect show dose dependency. Compound 2 gives the best activity, shows a tumor inhibition rate significantly higher than that of the positive control drug (Compound 61) at

TABLE 3

Experimental results of tumor inhibition of the present compounds at a single dose on human ovarian cancer SK-OV-3 transplanted tumor in nude mice model

| Group | $d_0$ | | $d_{21}$ | | | | Rate of tumor inhibition $d_{21}$ (%) | P | Animal number in each group | |
|---|---|---|---|---|---|---|---|---|---|---|
| | $V_{avg}$ (mm$^3$) | SD | $V_{avg}$ (mm$^3$) | SD | RTV | SD | | | Total | Partial regression |
| Control | 124.4 | ±20.5 | 1298.6 | ±616.1 | 10.5 | ±4.8 | 0 | — | 10 | 0 |
| Compound 2 | 120.0 | ±22.5 | 173.0 | ±106.9 | 1.5 | ±0.9 | 86 | 0.001 | 6 | 2 |
| Compound 3 | 126.2 | ±21.6 | 334.8 | ±113.8 | 2.7 | ±0.8 | 75 | 0.002 | 6 | 0 |
| Compound 5 | 134.1 | ±14.9 | 770.9 | ±118.5 | 5.8 | ±0.7 | 45 | 0.033 | 6 | 0 |
| Compound 61 | 134.8 | ±18.9 | 291.0 | ±109.4 | 2.2 | ±0.9 | 79 | 0.001 | 6 | 1 |

The tumor inhibition activity test results on human ovarian cancer SK-OV-3 nude mice-transplanted tumor model show that the tumor inhibition rate of compound 2 is significantly higher than that of compound 61 (86% vs 79%), the second is Compound 3, which has an activity (tumor inhibition rate 75%) slightly lower than that of compound 61. Two animals of the group for Compound 2 showed tumor regression, while one animal of the control group (Compound 61) showed tumor regression.

3) Therapeutic Effects of the Present Compounds at Different Dosages on Human Ovarian Cancer SK-OV-3 Transplanted Tumor in Nude Mice:

Nude mice were subcutaneously inoculated with human ovarian cancer SK-OV-3 cells, after tumors grew to 60-150 mm$^3$, the animals were randomly divided into groups ($d_0$). Three groups were set for compound in 50 mg, 100 mg and 200 mg dosages, negative control group was given 200 mg/kg of solvent, positive control group (Compound 61) had a dose of 200 mg/kg, intragastrically administered, once per day for consecutive 21 days. The tumor volume, and body weight of mice were measured 3 times per week, and all data were recorded. The tumor volume, relative tumor inhibition rate and so on were calculated according to the aforementioned methods. The results of test are shown in the following table:

equivalent dosages, and could achieve effective inhibition on tumor (tumor inhibition rate: 64%) at a dosage of 100 mg/kg.

The above results show that the compounds of the present invention have good tumor inhibition effects on tumors driven by tyrosine kinase.

D) Evaluation of the Pharmacokinetics of Compound 2

8 Healthy SD rats, male, body weight 200-220 g, were randomly divided into 2 groups (4 in each group), intragastrically administered single dose of compound 2 and compound 61 respectively, both at a dosage of 100 mg/kg, drug volume for administration was 10 ml/kg, and all drugs were formulated with 10% Tween-80 together with 90% deionized water. The animals were fasted for 12 h before test, drinking water freely. And fed after 2 h of administration. At 0.25, 0.5, 1.0, 2.0, 3.0, 5.0, 7.0, 9.0, 12 and 24 h after administration, 0.3 ml blood samples were taken from venous plexus behind eyeball of rats into heparinized test tubes, then centrifuged at 11000 rpm for 5 min, plasma were separated, and preserved at 20° C. The concentrations of drug in original form and metabolites thereof in plasma were measured by liquid chromatography-mass spectrometry. The results are shown in Table 5:

TABLE 4

Experimental results of tumor inhibition of the present compounds at different dosages on human ovarian cancer SK-OV-3 transplanted tumor in nude mice model

| Group | $d_0$ | | $d_{21}$ | | | | Rate of tumor inhibition $d_{21}$ (%) | P | Animal number in each group | |
|---|---|---|---|---|---|---|---|---|---|---|
| | $V_{avg}$ (mm$^3$) | SD | $V_{avg}$ (mm$^3$) | SD | RTV | SD | | | Total | Partial regression |
| Control | 123.2 | ±23.1 | 1254.0 | ±558.4 | 10.1 | ±3.7 | 0 | — | 10 | 0 |
| Compound 2 (50 mg/kg) | 129.4 | ±17.3 | 793.0 | ±411.7 | 6.0 | ±2.8 | 40 | 0.037 | 6 | 0 |
| Compound 2 (100 mg/kg) | 123.3 | ±15.5 | 438.4 | ±146.4 | 3.7 | ±1.6 | 64 | 0.001 | 6 | 0 |
| Compound 2 (200 mg/kg) | 129.5 | ±14.0 | 215.8 | ±95.0 | 1.6 | ±0.7 | 84 | 0.000 | 6 | 1 |
| Compound 3 (50 mg/kg) | 130.6 | ±44.2 | 830.7 | ±127.1 | 6.9 | ±2.3 | 32 | 0.077 | 6 | 0 |
| Compound 3 (100 mg/kg) | 120.2 | ±19.3 | 778.6 | ±173.5 | 6.5 | ±1.2 | 36 | 0.039 | 6 | 0 |
| Compound 3 (200 mg/kg) | 138.4 | ±10.7 | 612.6 | ±166.9 | 4.4 | ±1.1 | 56 | 0.002 | 6 | 0 |
| Compound 61 (200 mg/kg) | 138.5 | ±16.8 | 350.1 | ±114.5 | 2.5 | ±0.6 | 75 | 0.000 | 6 | 0 |

TABLE 5

Pharmacokinetic parameters of the positive control and prototype

| Tested substance | Compound | |
|---|---|---|
| | Compound 61 *[1] | Compound 2 |
| $T_{max} \pm SD(h)$ | 2.5 ± 0.6 | 3.5 ± 1.0 |
| $C_{max} \pm SD(ng/ml)$ | 3902 ± 1208 | 8881 ± 2061 |
| $AUC_{0-t} \pm SD(ng \cdot h/ml)$ | 26908 ± 9085 | 50299 ± 12863 |
| $AUC_{0-\infty} \pm SD(ng \cdot h/ml)$ | 26921 ± 9092 | 53236 ± 12248 |
| $MRT \pm SD(h)$ | 5.52 ± 0.90 | 5.38 ± 0.59 |
| $T_{1/2} \pm SD(h)$ | 1.91 ± 0.45 | 2.32 ± 0.5 |

*[1] Positive control Compound 61 detected in plasma;

Compound 2 obviously has better absorption and bioavailability, and at the same dosage level, gives a maximum plasma concentration or area under the concentration-time curve by twice of that of positive control. As expressed in $AUC_{0-t}$ of prototype, Compound 2 has a relative bioavailability of 187% in comparison with Compound 61 control group.

E) Effects of Compound 2 on the hERG Potassium Currents

HEK293 cells were transfected with plasmids containing hERG cDNA by liposome transfection method, and the inhibition effects of compound 2 in different concentrations on the hERG potassium currents (IKr) expressed in vitro were observed by using whole cell patch clamp recording mode, and the analysis and comparison of differences of the drug on IKr effect were performed by using Compound 61 as positive control.

As for Compound 2, its semi-effective inhibition dose IC50 for IKr pulse current was 10.06±0.96 μM, and its semi-effective inhibition dose IC50 for tail current was about 9.24±0.33 μM. As for Compound 61, its semi-effective inhibition dosage level IC50 for IKr pulse current was 1.09±0.045 μM, and its semi-effective inhibition dosage level IC50 for tail current was about 0.98±0.40 μM.

As for the expressed in vitro hERG potassium ion channel, the inhibition strength of compound 2 on it was lower than that of compound 61. The above results show that Compound 2 has a better safety.

What is claimed is:

1. A compound of formula I:

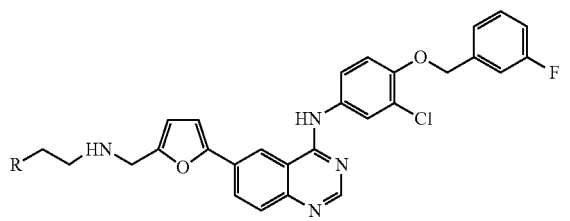

I or pharmaceutically acceptable salts thereof,
wherein,
R is a $C_{1-6}$-alkylsulfinyl, or a $C_{1-6}$alkylsulfinyl substituted with one or more halogens, or a $C_{1-6}$-alkylthio, or a $C_{1-6}$alkylthio substituted with one or more halogens, or a $C_{1-6}$-alkylamido, or a $C_{1-6}$-alkysulfonamido substituted with one or more halogens, or a group of formula

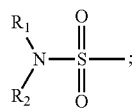

wherein $R_1$ and $R_2$ each are independently selected from the group consisting of hydrogen, a $C_{1-6}$-alkyl, and a $C_{1-6}$-alkyl substituted with one or more halogens.

2. The compound of formula I according to claim 1, wherein R is a $C_{1-6}$-alkylsulfinyl, or a $C_{1-6}$-alkylsulfinyl substituted with one or more halogens.

3. The compound of formula I according to claim 1, wherein R is a $C_{1-6}$-alkylthio, or a $C_{1-6}$-alkylthio substituted with one or more halogens.

4. The compound of formula I according to claim 1, wherein R is a $C_{1-6}$-alkylamido, a $C_{1-6}$-alkylsulfonamido, or a $C_{1-6}$-alkylsulfonamido substituted with one or more halogens.

5. The compound of formula I according to claim 1, wherein R is a $C_{1-4}$-alkylsulfinyl, a $C_{1-4}$-alkylsulfinyl substituted with 1 to 3 halogens, a $C_{1-4}$-alkylthio, a $C_{1-6}$-alkylthio substituted with 1 to 3 halogens, a $C_{1-4}$-alkylamido, a $C_{1-4}$-alkylsulfonamido, a $C_{1-4}$-alkylsulfonamido substituted with 1 to 3 halogens, a $C_{1-4}$-alkylsulfonyl substituted with 1 to 3 halogens, or a group of formula

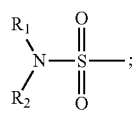

wherein $R_1$ and $R_2$ each are independently selected from the group consisting of hydrogen, a $C_{1-4}$-alkyl, and a $C_{1-4}$-alkyl substituted with 1 to 3 halogens.

6. The compound of formula I according to any one of claims 1 to 5, which is selected from the group consisting of:

N-(4-(3-fluorobenzyloxy)-3-chlorophenyl)-6-(5-((2-(sulfamoyl(ethylamino)methyl)-2-furyl)-quinazolin-4-amine;

N-(4-(3-fluorobenzyloxy)-3-chlorophenyl)-6-(5-((2-(methylsulfinyl)ethylamino)methyl)-2-furyl)-quinazolin-4-amine;

N-(4-(3-fluorobenzyloxy)-3-chlorophenyl)-6-(5-((2-(methylthio)ethylamino)methyl)-2-furyl)-2-furyl)-quinazolin-4-amine;

N-(4-(3-fluorobenzyloxy)-3-chlorophenyl)-6-(5-((2-(methanesulfonamido)ethylamino)methyl)-2-furyl)-quinazolin-4-amine;

N-(4-(3-fluorobenzyloxy)-3-chlorophenyl)-6-(5-((2-(trifluoromethylthio)ethylamino)methyl)-2-furyl)-quinozolin-4-amine;

N-(4-(3-fluorobenzyloxy)-3-chlorophenyl)-6-(5-((2-(trifluoromethylsulfinyl)ethylamino)methyl)-2-furyl)-quinazolin-4-amine;

N-(4-(3-fluorobenzyloxy)-3-chlorophenyl)-6-(5-((2-(2,2,2-trifluoroethylthio)ethylamino)methyl)-2-furyl)-quinozolin-4-amine;

N-(4-(3-fluorobenzyloxy)-3-chlorophenyl)-6-(5-((2-(2,2,2-trifluoroethylsulfinyl)ethylamino)methyl)-2-furyl)-quinazolin-4-amine;

N-(4-(3-fluorobenzyloxy)-3-chlorophenyl)-6-(5-((2-(acetamido)ethylamino)methyl)-2-furyl)-quinazolin-4-amine;

N-(4-(3-fluorobenzyloxy)-3-chlorophenyl)-6-(5-((2-(N-methylsulfamoyl)ethylamino)methyl)-2-furyl)-quinazolin-4-amine;

N-(4-(3-fluorobenzyloxy)-3-chlorophenyl)-6-(5-((2-(N-ethylsulfamoyl)ethylamino)methyl)-2-furyl)-quinazolin-4-amine; and N-(4-(3-fluorobenzyloxy)-3-chlorophenyl)-6-(5-((2-(2,2,2-trifluoroethylsulfonamido)ethylamino)methyl)-2-furyl)-quinazolin-4-amine;

or pharmaceutically acceptable salts thereof.

7. The compound according to formula I of claim 1, wherein the halogen is fluorine.

8. The compound according to formula I of claim 1, wherein the R is $C_{1-4}$-alkylsulfinyl or a $C_{1-4}$-alkylthio.

9. The compound according to formula I of claim 8, wherein R is $CH_3S$ or $CH_3S(O)$.

10. A pharmaceutical composition comprising a compound of formula I according to any one of claims 1 to 6, and one or more pharmaceutically acceptable carrier(s) or excipient(s).

11. A process for preparing a compound of formula I according to any one of claims 1 to 6, comprising:

a) reacting a compound of formula II,

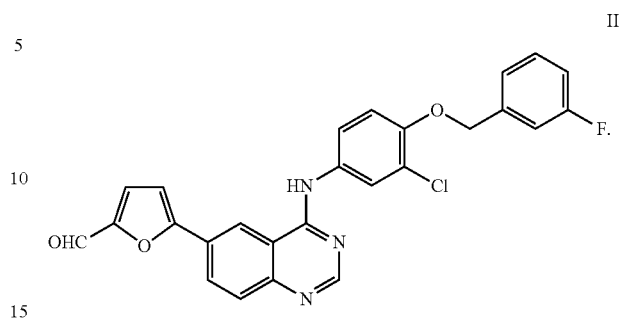

or a salt or reactive derivative thereof with a compound of formula III $$NH_2CH_2CH_2R \qquad III,$$

or an appropriate salt thereof in the presence of a suitable base and in a suitable solvent; and b) treating the reaction mixture of a) with a suitable reducing agent to give the compound of formula I.

12. A method for inhibiting EGFR and/or Her2 receptor tyrosine kinase activity in a mammal in need thereof, comprising administering the mammal a therapeutically effective amount of a compound of formula I according to any of the claims 1 to 6.

13. A method for inhibiting EGFR and/or Her2 kinase activity in a cell, comprising: contacting said cell with an effective amount of a compound of formula I according to any of claims 1 to 6, thereby inhibiting EGFR and/or Her2 kinase activity in said cell.

14. The method of claim 13, wherein the step of contacting takes place in vivo.

15. The method of claim 13, wherein the step of contacting takes place in vitro.

* * * * *